(12) United States Patent
Davis

(10) Patent No.: US 7,981,938 B2
(45) Date of Patent: *Jul. 19, 2011

(54) COLCHICINE COMPOSITIONS AND METHODS

(75) Inventor: Matthew W. Davis, Erwinna, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/687,406

(22) Filed: Jan. 14, 2010

(65) Prior Publication Data

US 2010/0105780 A1    Apr. 29, 2010

Related U.S. Application Data

(63) Continuation of application No. 12/545,377, filed on Aug. 21, 2009, which is a continuation of application No. 12/465,210, filed on May 13, 2009, and a continuation of application No. 12/407,980, filed on Mar. 20, 2009, which is a continuation of application No. 12/246,034, filed on Oct. 6, 2008.

(60) Provisional application No. 60/977,796, filed on Oct. 5, 2007, provisional application No. 61/090,965, filed on Aug. 22, 2008.

(51) Int. Cl.
*A01N 37/18* (2006.01)
*A61K 31/16* (2006.01)
*C07C 233/00* (2006.01)
*C07C 235/00* (2006.01)
*C07C 237/00* (2006.01)
*C07C 239/00* (2006.01)
*C07C 211/00* (2006.01)
*C07C 205/00* (2006.01)
*C07C 207/00* (2006.01)

(52) U.S. Cl. ........ 514/629; 564/123; 564/308; 564/427; 568/306

(58) Field of Classification Search .................. 514/629; 564/123, 308, 427; 568/306
See application file for complete search history.

(56) References Cited

U.S. PATENT DOCUMENTS 7,601,758 B1 * 10/2009 Davis ............................ 514/629
7,619,004 B1 * 11/2009 Davis ............................ 514/629

OTHER PUBLICATIONS

Wang et al. 2001, HMG-CoA reductase inhibitors (Statins) characterized as direct inhibitors of P-glycoprotein. Pharmaceutical Research, vol. 18, No. 6, pp. 800-806.*
Horn et al. 2006, Life-threatening colchicine drug interactions. Pharmacy Times, p. 111.*
U.S. Appl. No. 12/372,046, filed Feb. 2009, Davis, Matthew W.*
U.S. Appl. No. 12/407,980, filed Mar. 2009, Davis, Matthew W.*
U.S. Appl. No. 12/465,210, filed May 2009, Davis, Matthew W.*
U.S. Appl. No. 12/688,038, filed Jan. 2010, Davis, Matthew W.*
U.S. Appl. No. 12/576,355, filed Oct. 2009, Davis, Matthew W.*
U.S. Appl. No. 12/545,120, filed Aug. 2009, Davis, Matthew W.*
U.S. Appl. No. 12/489,750, filed Jun. 2009, Davis, Matthew W.*
U.S. Appl. No. 12/545,377, filed Aug. 2009, Davis, Matthew W.*
U.S. Appl. No. 12/246,034, filed Oct. 2008, Davis, Matthew W.*
Jordan, K.M. et al. "British Society for Rheumatology and British Health Professionals in Rheumatology Guideline for the Management of Gout (Full Guidelines)", Rheumatology, 2007, pp. 1-17, Online Supplement to Jordan et al. 2007 "British Society for Rheumatology and British Health Professionals in Rheumatology Guideline for the Management of Gout (Executive Summary)", Rheumatology (Oxford). Aug. 2007;46(8):1372-4. Epub May 23, 2007.
Zhang, W. et al., "EULAR evidence based recommendations for gout. Part II: Management. Report of a task force of the EULAR Standing Committee for International Clinical Studies Including Therapeutics (ESCISIT)", Ann Rheum Dis 2006, 65: 1312-1324.
Ahern, M.J. et al., "Does Colchicine Work? The results of the first controlled study in acute gout" Aust NZ J Med 1987; 17: 301-304.
Borstad, G.C. et al., "Colchicine for prophylaxis of acute flares when initiating allopurinol for chronic gouty arthritis" J Rheumatol 2004; 31: 2429-32.
Terkeltaub, R.A, "Gout", N.E. J Med 2003, 349: 1647-55.
Paulus, H.E. et al. "Prophylactic colchicine therapy of intercritical gout. A placebo-controlled study of probenecid-treated patients" Arthritis Rheum 1974, 17(5): 609-14.
Probenecid and Colchicine Tablets USP, Mar. 2006, Watson Laboratories product label.
Colchicine Tablets USP, 0.6 mg, Vision Pharma LLC product label, Oct. 2006.
Leikin, J.B. and Paloucek, F.P., eds.; Poisoning and Toxicology Handbook, 4th Ed., CRC Press, Taylor & Francis Group, Informa Healthcare, Aug. 2007, pp. 216-217.
Yu, T.F. & Gutman, A.B., "Efficacy of Colchicine Prophylaxis in Gout: Prevention of Recurrent Gouty Arthritis Over a Mean Period of Five Years in 208 Gouty Subjects", Ann. Int. Med., Aug. 1961, 55(2): pp. 179-192.
"Abate" entry, Merriam-Webster Online Dictionary, downloaded from http://www.merriam-webster.com/dictionary/abate on Nov. 18, 2010.
Ben-Chetrit, E. et al., Colchicine: 1998 Update, Semin Arthritis Rheum. 1998; 28: 48-59.
FDA Alert issued Jul. 30, 2009, "Information for Healthcare Professionals: New Safety Information for Colchicine (marketed as Colcrys)", downloaded from the FDA internet website (http://www.fda.gov/Drugs/DrugSafety/PostmarketDrugSafetyInformationfor PatientsandProviders/DrugSafetyInformationforHeathcareProfessionals/ucm174315.htm) on Sep. 8, 2010.

* cited by examiner

Primary Examiner — Sreeni Padmanabhan
Assistant Examiner — Kara R McMillian
(74) Attorney, Agent, or Firm — Cantor Colburn LLP

(57) ABSTRACT

Stable ultrapure colchicine compositions comprising ultrapure colchicine and a pharmaceutically acceptable excipient are described. The compositions can be tablets. Methods for preparing such compositions and methods of use are also disclosed. Methods of treating gout flares with colchicine compositions are also disclosed.

1 Claim, 1 Drawing Sheet

COLCHICINE COMPOSITIONS AND METHODS

CROSS REFERENCE TO RELATED APPLICATION

This application is a continuation of U.S. application Ser. No. 12/545,377, filed Aug. 21, 2009; which is a continuation of U.S. application Ser. No. 12/465,210, filed May 13, 2009, and a continuation of U.S. application Ser. No. 12/407,980, filed Mar. 20, 2009, which is a continuation of U.S. application Ser. No. 12/246,034, filed Oct. 6, 2008, which claims the benefit of U.S. Provisional Application Ser. No. 60/977,796 filed Oct. 5, 2007 and U.S. Provisional Application Ser. No. 61/090,965 filed Aug. 22, 2008; each of the above-named applications is hereby incorporated by reference in its entirety.

BACKGROUND

This application relates to colchicine compositions for therapeutic purposes, specifically ultrapure colchicine, and methods of making and using the colchicine compositions.

Colchicine, chemical name (−)-N-[7S,12aS)-1,2,3,10-tetramethoxy-9-oxo-5,6,7,9-tetrahydrobenzo[a]heptalen-7-yl]-acetamide, is a pale yellow powder soluble in water in 1:25 dilution.

Colchicine is an alkaloid found in extracts of certain plants such as *Colchicum autumnale* and *Gloriosa superba*. Colchicine arrests cell division in animals and plants. It has adversely affected spermatogenesis in humans and in some animal species under certain conditions.

Gout (or gouty arthritis) is a disease caused by a build up of uric acid due to an overproduction of uric acid or a reduced ability of the kidney to get rid of uric acid. It is more common in males, postmenopausal women, and people with high blood pressure. Heavy alcohol use, diabetes, obesity, sickle cell anemia, and kidney disease also increase the risk. The condition may also develop in people who take drugs that interfere with uric acid excretion.

In gout, monosodium urate or uric acid crystals are deposited on the articular cartilage of joints, tendons, and surrounding tissues due to elevated concentrations of uric acid in the blood stream. This provokes an inflammatory reaction of these tissues. Gout is characterized by excruciating, sudden, unexpected, burning pain, as well as swelling, redness, warmness, and stiffness in the affected joint. Low-grade fever may also be present. The patient usually suffers from two sources of pain. The crystals inside the joint cause intense pain whenever the affected area is moved. The inflammation of the tissues around the joint also causes the skin to be swollen, tender and sore if it is even slightly touched. For example, a blanket or even the lightest sheet draping over the affected area could cause extreme pain.

Acute gouty arthritis (alternatively referred to as a gout flare or a gout attack) is a sudden attack of pain in affected joints, especially in the feet and legs. Chronic gout involves repeated attacks of joint pain.

In acute gouty arthritis, symptoms develop suddenly and usually involve only one or a few joints. The big toe, knee, or ankle joints are most often affected. The pain frequently starts during the night and is often described as throbbing, crushing, or excruciating. The joint appears infected with signs of warmth, redness, and tenderness. The attacks of painful joints may go away in several days, but may return from time to time. Subsequent attacks usually last longer. Some people may progress to chronic gout (chronic gouty arthritis), while others may have no further attacks.

If several attacks of gout occur each year, it can lead to joint deformity and limited motion in joints. Uric acid deposits, called tophi, develop in cartilage tissue, tendons, and soft tissues. These tophi usually develop only after a patient has suffered from the disease for many years. Deposits also can occur in the kidneys, leading to chronic kidney failure.

Colchicine can be used for treating adults with acute gouty arthritis and pain in attacks of acute gouty arthritis, and also can be used beneficially for treating adults with chronic gout for prophylaxis of acute gout flares. Although its exact mode of action in the relief of gout is not completely understood, colchicine is known to decrease the inflammatory response to urate crystal deposition by inhibiting migration of leukocytes, to interfere with urate deposition by decreasing lactic acid production by leukocytes, to interfere with kinin formation and to diminish phagocytosis and the subsequent anti-inflammatory response. The anti-inflammatory effect of colchicine is relatively selective for acute gouty arthritis. However, other types of arthritis occasionally respond. It is neither an analgesic nor a uricosuric and will not prevent progression to chronic gouty arthritis. It does have a prophylactic, suppressive effect that helps to reduce the incidence of acute attacks and to relieve the residual pain and mild discomfort that patients with gout occasionally experience. In some instances, non-steroidal anti-inflammatory drugs (NSAIDs) may also be prescribed to relieve pain and inflammation in acute gouty arthritis attacks. Strong painkillers, such as codeine, or corticosteroids may also be prescribed to relieve the pain.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10 to 20% eliminated unchanged in the urine.

There remains a need for pure forms of colchicine having low levels of impurities for pharmaceutical use to minimize the potential for side effects in patients taking colchicine pharmaceutical products and to minimize the need for costly toxicity testing required for approval of pharmaceutical products comprising conventional colchicine having high levels of individual or total impurities. In particular, there is a need for stable compositions comprising ultrapure colchicine.

SUMMARY

Disclosed herein are colchicine compositions.

In one embodiment, the colchicine composition comprises ultrapure colchicine, wherein the ultrapure colchicine comprises no more than about 3.0% total impurities, specifically no more than about 2.0% total impurities, and a pharmaceutically acceptable excipient.

In another embodiment, the colchicine composition comprises ultrapure colchicine, wherein the ultrapure colchicine comprises no more than 3.0% total impurities, specifically no more than about 2.0% total impurities, a filler, a binder, and a disintegrant.

In yet another embodiment, the colchicine composition comprises about 0.6 mgA colchicine, about 12 to about 16 mg pregelatinized starch, about 20 to about 24 mg microcrystalline cellulose, about 3.9 to about 4.7 mg sodium starch glycolate, about 0.5 to about 0.7 mg magnesium stearate, and an amount of lactose monohydrate such that the colchicine dosage form has a total weight of about 100 mg.

In an embodiment, the colchicine composition comprises colchicine; and a pharmaceutically acceptable excipient; wherein the colchicine composition comprises no more than about 3.5% total impurities and no more than 0.42% N-deacetyl-N-formyl colchicine.

In an embodiment, the colchicine composition comprises colchicine; and a pharmaceutically acceptable excipient, wherein the colchicine composition has 0.6 mgA colchicine, wherein a single dose of the 0.6 mgA colchicine composition has enhanced bioavailability as compared to a single dose of a pharmaceutical product comprising 0.5 mg colchicine after potency correction for colchicine.

In an embodiment, the colchicine composition comprises colchicine; and a pharmaceutically acceptable excipient, wherein the colchicine composition has equivalent bioavailability when administered in a fed or a fasted state.

In an embodiment, the colchicine composition comprises colchicine; and a pharmaceutically acceptable excipient, wherein administration of a single dose of the colchicine composition to a human provides a Cmax between about 1.3 ng/mL and about 4.0 ng/mL, an $AUC_{0-t}$ between about 4.4 ng-hr/mL and about 30.8 ng-hr/mL, or an $AUC_{0-INF}$ between about 6.7 ng-hr/mL and about 27.8 ng-hr/mL.

Methods of making the colchicine compositions are also disclosed herein.

In an embodiment, the method comprises wet granulating ultrapure colchicine, wherein the ultrapure colchicine comprises no more than about 3.0% of total impurities, with a pharmaceutically acceptable excipient to obtain wet granules, and mixing the granules with a disintegrant to obtain the composition.

In yet another embodiment, the method comprises wet granulating colchicine with a pharmaceutically acceptable excipient to obtain wet granules; drying the wet granules to obtain dried granules; milling the dried granules to obtain milled granules; mixing the milled granules with a disintegrant to obtain the composition; mixing the composition with a lubricant to obtain a tableting blend; and compressing the tableting blend to obtain a colchicine tablet.

Also disclosed herein are methods of making ultrapure colchicine.

In an embodiment, the method comprises subjecting colchicine comprising more than about 3.0% total impurities to column chromatography to obtain a colchicine concentrate, distilling the colchicine concentrate to obtain a colchicine distillate, and crystallizing ultrapure colchicine from the colchicine distillate; wherein the ultrapure colchicine comprises no more than about 3.0% total impurities.

In another embodiment, the method comprises subjecting colchicine comprising more than about 3.0% total impurities to neutral alumina column chromatography to obtain a colchicine concentrate; distilling the colchicine concentrate with ethyl acetate to obtain a colchicine distillate; and crystallizing ultrapure colchicine from the colchicine distillate in ethyl acetate; wherein the ultrapure colchicine comprises no more than about 3.0% total impurities.

In still another embodiment, the method comprises subjecting colchicine comprising more than about 3.0% total impurities to neutral alumina column chromatography to obtain a colchicine concentrate; distilling the colchicine concentrate with ethyl acetate to obtain a colchicine distillate; crystallizing a purified colchicine from the colchicine distillate in ethyl acetate; washing the purified colchicine with ethyl acetate to obtain a washed purified colchicine; and drying the washed purified colchicine to obtain ultrapure colchicine, wherein the ultrapure colchicine comprises no more than about 3.0% total impurities.

Also disclosed are methods of treating a patient with the colchicine compositions.

In an embodiment, the method comprises administering a dosing regimen to a patient having an acute gouty arthritis attack, wherein the dosing regimen consists of two colchicine dosage forms at the onset of the acute gouty arthritis attack, followed by one colchicine dosage form in about one hour, wherein a colchicine dosage form comprises about 0.6 mgA colchicine.

In an embodiment, the method comprises administering less than about 2 mg of colchicine to a patient over a period of about one hour, wherein the patient is experiencing an acute gouty arthritis attack.

In an embodiment, the method comprises administering to a human experiencing an acute gouty arthritis attack a colchicine composition, wherein the composition is effective to provide a colchicine plasma concentration profile having an area under the plasma colchicine concentration curve from time 0 to infinity ($AUC_{0-INF}$) of about 34.2 ng-hr/mL to about 74.1 ng-hr/mL, an area under the plasma colchicine concentration curve from time 0 to time t ($AUC_{0-t}$) of about 28.8 ng-hr/mL to about 58.9 ng-hr/mL, or a maximum plasma colchicine concentration (Cmax) of about 3.2 ng/mL to about 11.4 ng/mL for a maximum total dose of about 1.8 mg colchicine.

In an embodiment, the method comprises administering a dosing regimen to a patient having an acute gouty arthritis attack, wherein the dosing regimen consists of two colchicine dosage forms at the onset of the acute gouty arthritis attack, followed by one colchicine dosage form in about one hour, wherein a colchicine dosage form comprises about 0.6 mgA colchicine, wherein the dosing regimen is effective to provide an area under the plasma colchicine concentration curve from time 0 to infinity ($AUC_{0-INF}$) of about 34.2 ng-hr/mL to about 74.1 ng-hr/mL, an area under the plasma colchicine concentration curve from time 0 to time t ($AUC_{0-t}$) of about 28.8 ng-hr/mL to about 58.9 ng-hr/mL, or a maximum plasma colchicine concentration (Cmax) of about 3.2 ng/mL to about 11.4 ng/mL.

In an embodiment, the method comprises administering a dosing regimen to a patient having an acute gouty arthritis attack, wherein the dosing regimen consists of two colchicine dosage forms at the onset of the acute gouty arthritis attack, followed by one colchicine dosage form in about one hour, wherein a colchicine dosage form comprises about 0.6 mgA colchicine, wherein the dosing regimen is effective to provide a colchicine plasma concentration profile which has a maximum plasma colchicine concentration (Cmax) which is at least 80% of plasma Cmax provided by a dosing regimen of two dosage forms, followed by one dosage form about every hour later for 6 hours.

In an embodiment, the method comprises administering a dosing regimen to a patient having an acute gouty arthritis attack, wherein the dosing regimen consists of two colchicine dosage forms at the onset of the acute gouty arthritis attack, followed by one colchicine dosage form in about one hour, wherein a colchicine dosage form comprises about 0.6 mgA colchicine, wherein the odds of a patient being a responder to the dosing regimen are not statistically different from the odds of being a responder to a second dosing regimen consisting of two colchicine dosage forms at the onset of the acute gouty arthritis attack, followed by one colchicine dosage form every hour for 6 hours, wherein a responder is a patient obtaining a ≧50% improvement in pain at 24 hours after the first dose, without taking an additional active agent for reducing pain of the acute gouty arthritis attack.

In an embodiment, the method comprises administering a dosing regimen to a patient having an acute gouty arthritis attack, wherein the dosing regimen consists of two colchicine dosage forms at the onset of the acute gouty arthritis attack, followed by one colchicine dosage form in about one hour, wherein a colchicine dosage form comprises about 0.6 mgA colchicine, wherein in a randomized, placebo-controlled study of the dosing regimen in patients with an acute gouty arthritis attack, the fraction of patients that experienced a given % improvement in pain at 24 hrs after first dose is shown in FIG. 1.

These and other embodiments, advantages and features of the present invention become clear when detailed description and examples are provided in subsequent sections.

DETAILED DESCRIPTION

Figure 1:
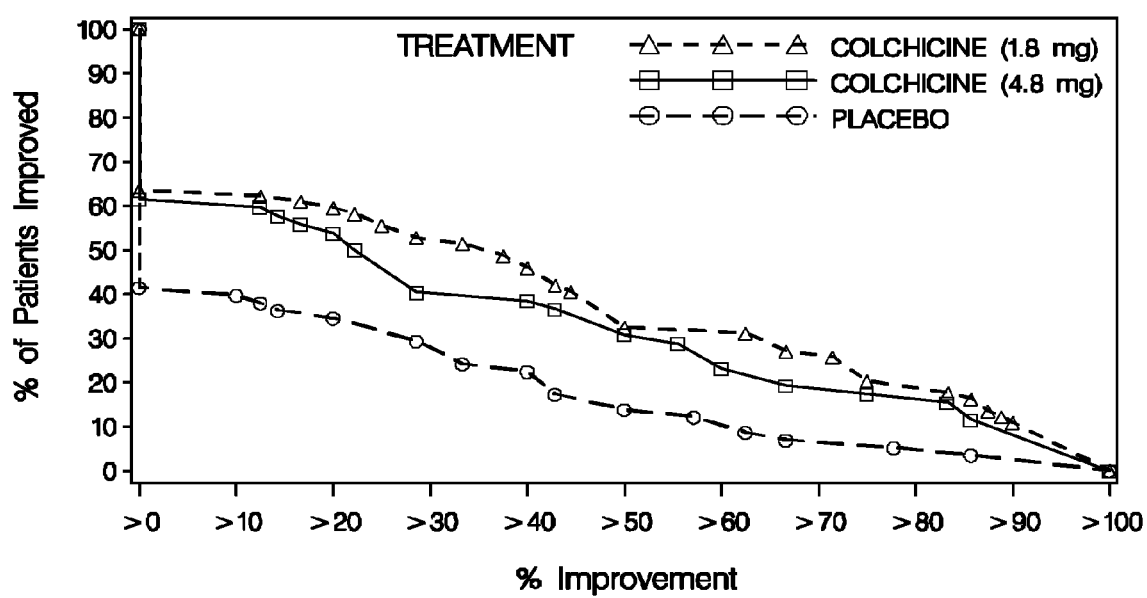
FIG. 1 shows the fraction of all patients improved at 24 hrs post-first dose of colchicine, regardless of pain rescue, as a function of the percent improvement in pain determined in the study of Example 3.

Disclosed herein are compositions comprising ultrapure colchicine and a pharmaceutically acceptable excipient. Herein, "ultrapure colchicine" means colchicine comprising no more than about 3.0% of total impurities, measured chromatographically as described below, specifically the ultra pure colchicine comprises no more than about 2.0% of total impurities, more specifically no more than about 1.0% of total impurities, or even more specifically no more than about 0.5% of total impurities. In some embodiments, the ultrapure colchicine comprises no more than about 0.10% of N-deacetyl-N-formyl colchicine, measured chromatographically. In some embodiments, the ultrapure colchicine is purified from a botanical source. Methods of making ultrapure colchicine and the compositions comprising the ultrapure colchicine, methods of treating various conditions using the compositions. Dosing regimens are also disclosed.

Not wishing to be bound by theory, it is postulated that the properties of colchicine as an antimitotic agent (e.g. its tubulin binding properties) or its effects on Pgp transporter properties provide the therapeutic effects of colchicine described herein. The methods described herein therefore also contemplate the use of an antimitotic agent with at least one pharmaceutically acceptable excipient. An antimitotic agent can be a drug that prevents or inhibits mitotis, or cell division.

In the specification and claims that follow, references will be made to a number of terms which shall be defined to have the following meaning.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to") unless otherwise noted.

An "active agent" means a compound (including for example, colchicine), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates), and co-crystals of the free compound or salt, crystalline forms, non-crystalline forms, and any polymorphs of the compound are contemplated herein. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral HPLC column. All forms are contemplated herein regardless of the methods used to obtain them.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

"Bioequivalence" or "equivalent bioavailability" means the absence of a significant difference in the rate or extent to which the active agent in pharmaceutical equivalents or pharmaceutical alternatives is absorbed into a living system or is made available at the site of physiological activity or the absence of a significant difference in the rate or extent to which the active agent in a pharmaceutical composition is absorbed into a living system or is made available at the site of physiological activity when administered by two different methods (e.g., dosing under non-fasted versus fasted conditions). Bioequivalence can be determined by comparing in vitro dissolution testing data for two dosage forms or two dosing conditions or by comparing pharmacokinetic parameters for two dosage forms or two dosing conditions.

In some embodiments, two products (e.g. an inventive composition and COL-PROBENECID®) or two methods (e.g., dosing under fed (non-fasted) versus fasted conditions) are bioequivalent if the ratio of the geometric mean of logarithmic transformed $AUC_{0-\infty}$, $AUC_{0-t}$, or $C_{max}$ for the two products or two methods is about 0.80 to about 1.25; specifically if the 90% Confidence Interval (CI) limit for the ratio of the geometric mean of logarithmic transformed $AUC_{0-\infty}$, $AUC_{0-t}$, or $C_{max}$ for the two products or two methods is about 0.80 to about 1.25; more specifically if the ratios of the geometric mean of logarithmic transformed $AUC_{0-\infty}$, $AUC_{0-t}$, and $C_{max}$ for the two products or two methods are about 0.80 to about 1.25; yet more specifically if the 90% Confidence Interval (CI) limits for the ratios of the geometric mean of logarithmic transformed $AUC_{0-\infty}$, $AUC_{0-t}$, and $C_{max}$ for the two products or two methods are about 0.80 to about 1.25.

"Colchicine therapy" refers to medical treatment of a symptom, disorder, or condition by administration of colchicine. Colchicine therapy can be considered optimal when effective plasma levels are reached when required. In addition, peak plasma values ($C_{max}$) should be as low as possible so as to reduce the incidence and severity of possible side effects.

"Conventional colchicine" means colchicine comprising more than 3% but no more than about 5.0% total impurities, measured chromatographically as described below, and comprising more than about 0.10% of N-deacetyl-N-formyl colchicine.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Dosing regimen" means the dose of an active agent taken at a first time by a patient and the interval (time or symptomatic) at which any subsequent doses of the active agent are taken by the patient. The additional doses of the active agent can be different from the dose taken at the first time.

A "dose" means the measured quantity of an active agent to be taken at one time by a patient.

"Efficacy" means the ability of an active agent administered to a patient to produce a therapeutic effect in the patient.

As used herein, the term "mgA" refers to milligrams of the active colchicine, or the free base of colchicine, after compensating for the potency of the batch of colchicine (i.e., after compensating for impurities, including solvents, and salts in the colchicine). For example, 0.612 mg of an ultrapure colchicine free base having a total impurity of 2 wt % (thus a purity of 98 wt %) contains 0.6 mgA (0.612 mg×0.98=0.6 mgA) of colchicine.

An "oral dosage form" means a unit dosage form for oral administration.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

"Pharmaceutically acceptable" means that which is generally safe, non-toxic and neither biologically nor otherwise undesirable and includes that which is acceptable for veterinary use as well as human pharmaceutical use.

"Pharmaceutically acceptable salts" includes derivatives of colchicine, wherein the colchicine is modified by making acid or base addition salts thereof, and further refers to pharmaceutically acceptable solvates, including hydrates, and co-crystals of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the colchicine. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparaginate, glutamate, and the like; and combinations comprising one or more of the foregoing salts; organic amine salts such as triethylamine salt, pyridine salt, picoline salt, ethanolamine salt, triethanolamine salt, dicyclohexylamine salt, N,N' dibenzylethylenediamine salt, and the like; and amino acid salts such as arginate, asparaginate, glutamate, and the like; and combinations comprising one or more of the foregoing salts. All forms of such derivatives of colchicine are contemplated herein, including all crystalline, amorphous, and polymorph forms. Specific colchicine salts include colchicine hydrochloride, colchicine dihydrochloride, and co-crystals, hydrates or solvates thereof.

"Pharmacokinetic parameters" describe the in vivo characteristics of an active agent (or a metabolite or a surrogate marker for the active agent) over time, such as plasma concentration (C), $C_{max}$, $C_n$, $C_{24}$, $T_{max}$, and AUC. "$C_{max}$" is the measured plasma concentration of the active agent at the point of maximum, or peak, concentration. "$C_{min}$" is the measured plasma concentration of the active agent at the point of minimum concentration. "$C_n$" is the measured plasma concentration of the active agent at about n hours after administration. "$C_{24}$" is the measured plasma concentration of the active agent at about 24 hours after administration. The term "$T_{max}$" refers to the time at which the measured plasma concentration of the active agent is the highest after administration of the active agent. "AUC" is the area under the curve of a graph of the measured plasma concentration of an active agent vs. time, measured from one time point to another time point. For example $AUC_{0-t}$ is the area under the curve of plasma concentration versus time from time 0 to time t, where t can be the last time point with measurable plasma concentration for an individual formulation. The $AUC_{0-\infty}$ or $AUC_{0-INF}$ is the calculated area under the curve of plasma concentration versus time from time 0 to time infinity. In steady-state studies, $AUC_{0-\tau}$ is the area under the curve of plasma concentration over the dosing interval (i.e., from time 0 to time $\tau$ (tau), where tau is the length of the dosing interval. Other pharmacokinetic parameters are the parameter $K_e$ or $K_{el}$, the terminal elimination rate constant calculated from a semi-log plot of the plasma concentration versus time curve; $t_{1/2}$ the terminal elimination half-life, calculated as $0.693/K_{el}$; CL/F denotes the apparent total body clearance after administration, calculated as Total Dose/Total $AUC_\infty$; and $V_{area}/F$ denotes the apparent total volume of distribution after administration, calculated as Total Dose/(Total $AUC_\infty \times K_{el}$).

"Adverse event" means any untoward medical occurrence in a patient administered an active agent and which does not necessarily have to have a causal relationship with this treatment. An adverse event (AE) can therefore be any unfavorable and unintended sign (including an abnormal laboratory finding, for example), symptom, or disease temporally associated with the use of the active agent, whether or not considered related to the active agent.

"Side effect" means a secondary effect resulting from taking an active agent. The secondary effect can be a negative (unfavorable) effect (i.e., an adverse side effect) or a positive (favorable) effect.

The most frequently reported adverse side effects to colchicine therapy are gastrointestinal, specifically diarrhea; abdominal pain with cramps; nausea; and vomiting. Less frequently or rarely reported adverse side effects associated with colchicine therapy include anorexia, agranulocytosis, allergic dermatitis, allergic reactions, alopecia, angioedema, aplastic anemia, bone marrow depression, myopathy, neuropathy, skin rash, thrombocytopenic disorder, and urticaria.

Determining that a patient experiences an adverse side effect can be performed by obtaining information from the patient regarding onset of certain symptoms which may be indicative of the adverse side effect, results of diagnostic tests indicative of the adverse side effect, and the like.

Ultrapure colchicine comprising low levels of individual impurities or total impurities is highly desirable as compared to conventionally available forms of colchicine. Currently, commercially available forms of colchicine often comprise high levels of impurities. Depending on the source or the preparation process, colchicine may comprise some or all of the common impurities shown in Table 1.

The ultrapure colchicine disclosed herein comprises no more than (NMT) about 3.0%; specifically NMT about 2.0%, or more specifically, NMT about 1.0%, or even more specifically NMT about 0.5% of total impurities. In one embodiment, "total impurities" includes the common impurities, Impurities A through F, as well as all structurally unidentified impurities eluting within 1.5 times the retention time of colchicine using an HPLC method as described in more detail below. In another embodiment, other HPLC and HPLC meth-

TABLE 1

| Common Impurities | Chemical Name | Other common name |
|---|---|---|
| Impurity A | N-[(7S,12aS)1,2,3,10-tetramethoxy-9-oxo-5,6,7,9-tetrahydrobenzo[a]heptalen-7-yl]formamide | N-deacetyl-N-formyl colchicine |
| Impurity B | (−)-N-[(7S,12aR)-1,2,3,10-tetramethoxy-9-oxo-5,6,7,9-tetrahydrobenzo[a]heptalen-7-yl]-acetamide | Conformational isomer |
| Impurity C | N-[(7S,7bR,10aS)-1,2,3,9-tetramethoxy-8-oxo-5,6,7,7b,8,10a-hexahydrobenzo[a]cyclopenta[3,4]cyclobuta[1,2-c]cyclohepten-7-yl]-acetamide | β-Lumicolchicine |
| Impurity D | N-[(7S,12aS)-3-(β-D-glucopyranosyloxy)-1,2,10-trimethoxy-9-oxo-5,6,7,9-tetrahydrobenzo[a]heptalen-7-yl]-acetamide | Colchicoside |
| Impurity E | N-[(7S,12aS)-3-hydroxy-1,2,10-trimethoxy-9-oxo-5,6,7,9-tetrahydrobenzo[a]heptalen-7-yl]-acetamide | 3-O-demethyl colchicine |
| Impurity F | N-[7S,12aS)-10-hydroxy-1,2,3-trimethoxy-9-oxo-5,6,7,9-tetrahydrobenzo[a]heptalen-7-yl]acetamide | Colchiceine |

In addition to the common impurities listed above, colchicine may also comprise N-[(7S,12aS)-2-hydroxy-1,3,10-trimethoxy-9-oxo-5,6,7,9-tetrahydrobenzo[a]heptalen-7-yl]-acetamide ("2-O-demethyl colchicine") impurity. Some analytical methods cannot differentiate 2-O-demethyl colchicine from 3-O-demethyl colchicine.

In addition to the common impurities listed above, colchicine may also comprise other structurally unidentified impurities. In fact, conventional forms of colchicine may comprise as much as 5% of total impurities, determined chromatographically as described below. Such high levels of impurities in conventional colchicine pose several problems. The impurities may cause side effects in patients taking dosage forms comprising conventional colchicine. For example, N-deacetyl-N-formyl-colchicine (Impurity A, also known as Gloriosine) is tumorigenic and has been studied as an anticancer agent. Therefore reduction in the level of N-deacetyl-N-formyl colchicine found in convention colchicine is highly desirable. Additionally, high levels of impurities can also pose a regulatory challenge for pharmaceutical companies using conventional colchicine in products. For a pharmaceutical product comprising an active agent, the United States Food and Drug Administration (FDA) requires "qualification" or toxicity information for any impurity that is greater than the International Conference on Harmonization (ICH) qualification threshold of 0.15% per individual impurity in the active agent substance or 1.0% in the dosage form. Thus, there is a regulatory benefit for a pharmaceutical company to market pharmaceutical products comprising active agents comprising low levels of individual impurities or total impurities in the active agent substance as well as in the dosage form. As a result, for a pharmaceutical composition comprising colchicine, it is in the best interest of both the pharmaceutical company and the patient that impurities be minimized, if possible, in the colchicine and in colchicine compositions or dosage forms.

ods, for example, as described in more detail below, can be used to quantify the level of total impurities.

The ultrapure colchicine may also comprise low levels of individual impurities. In one embodiment, the ultrapure colchicine comprises NMT about 2.0%, specifically NMT about 1.5%; more specifically NMT about 1.0%; or yet more specifically, NMT about 0.5%, or even more specifically, NMT about 0.15%, or still more specifically, NMT about 0.10%, of any individual impurity. The impurity can be Impurity A, Impurity B, Impurity C, Impurity D, Impurity E, Impurity F, or an unidentified impurity.

In an embodiment, the ultrapure colchicine comprises no more than (NMT) about 3.0% total impurities and NMT about 0.10% N-deacetyl-N-formyl colchicine.

In another embodiment, the ultrapure colchicine comprises NMT about 3.0% total impurities; NMT about 0.1% per individual impurity of Impurity A, Impurity C, Impurity D, and Impurity E; NMT about 0.15% Impurity F; and NMT about 2.0% of Impurity B.

Not wishing to be bound by theory, it is postulated that the conformational isomer, Impurity B, is in equilibrium with the active colchicine such that even after purification of the colchicine to about 0.5% Impurity B, the purified colchicine re-equilibrates to a level of Impurity B around about 1% to about 1.3%.

The level of an individual impurity or of total impurities in colchicine may be determined by any suitable analytical method known in the art. In one embodiment, the impurity levels are determined using a high performance liquid chromatography (HPLC) assay, for example, the HPLC method described in the Colchicine Official Monograph USP30/NF25, herein fully incorporated by reference.

Exemplary conditions for HPLC or ultra performance liquid chromatography (HPLC) assays that can be used for the impurity analysis of colchicine or of a colchicine pharmaceutical product are listed in Table 2.

TABLE 2

Exemplary HPLC Conditions For Colchicine Purity Analysis

|  | USP30/NF25 Colchicine Official Monograph Method | HPLC Method | UPLC Method |
| --- | --- | --- | --- |
| Mobile phase | 0.5 Molar $KH_2PO_4$ in Methanol:Water (65:45, v:v), pH adjusted to 5.5 with $H_3PO_4$ | pH 7.2 10 mM Phosphate Buffer:methanol (MeOH) Gradient | pH 4.5 Ammonium Acetate Buffer:MeOH Gradient |
| Column | Octylsilyl silica gel, 4.6 mm × 25 cm, 5 micron | Zorbax SBC(18) 4.6 × 250 mm | Acquity GEH C18 2.1 × 100 mm, 1.7 um |
| Flow rate | 1.0 mL/min | 1.0 mL/min | 0.25 mL/min |
| Column Temp | Ambient | Ambient | 30 C. +/− 2 C. |
| Detection | 254 nanometers (nm) | 246 nm | 246 nm |
| Injection volume | 20 microliters (uL) | 75 uL | 7 uL |
| Sample Conc. | 0.006 mg/mL | 0.120 mg/ml | 0.012 mg/ml |
| Run time | 15 minutes (min) | 46 min | 25 min |

When using one of the above HPLC conditions in Table 2 for colchicine purity analysis, the relative retention time (RRT) of an impurity can be calculated by the following formula:

RRT of an impurity=RT of the impurity/RT of colchicine, where RT stands for retention time of the impurity or the colchicine at the particular conditions used in the assay.

In one embodiment, using the HPLC method in Table 2, the retention time (RT) of colchicine is about 7 minutes and the relative retention times (RRTs) of the common impurities eluting within 1.5 times the retention time for colchicine are listed in Table 2A:

TABLE 2A

Relative Retention Times (RRTs) of the Common Impurities

| Impurity ID | RRT |
| --- | --- |
| N-deacetyl-N-formyl colchicine - Impurity A | 0.94 |
| Conformational isomer - Impurity B | 0.8 |
| β-Lumicolchicine - Impurity C | 1.2 |
| Colchicoside - Impurity D | 0.4 |
| 3-O-demethyl colchicine - Impurity E | 0.7 |

In one embodiment, the percent of a particular impurity is calculated by dividing the response (peak area) of the impurity peak by the sum of all responses (total peak area of all peaks, including the colchicine peak and all common and unidentified impurity peaks) eluting within 1.5 times the retention time for colchicine in the HPLC assay and multiplying the result by 100%.

In one embodiment, the level (%) of total impurities is calculated by dividing the sum of responses of any peaks other than that due to colchicine eluting within 1.5 times the retention time for colchicine by the sum of all responses eluting in the HPLC assay and multiplying the result by 100%.

An additional HPLC method for determining the level of impurities other than Impurity F in colchicine or in colchicine pharmaceutical products has been developed and validated for use as an alternative to the methods in Table 2 above. The method is shown in Table 3A below.

TABLE 3A

Quantitative HPLC Method for determining all impurities other than impurity F in colchicine and colchicine pharmaceutical products.

|  | Quantitative HPLC Method for colchicine and colchicine products. |
| --- | --- |
| Mobile phase | pH 4.5 Ammonium Acetate Buffer:methanol Gradient |
| Column | Waters XBridge C18, 250 mm × 4.6 mm, 5 μm particle size |
| Flow rate | 0.9 mL/min |
| Column Temp | 10 ± 3.5 C. (for column)/10 ± 2 C. (for sample) |
| Detection | 246 nm |
| Injection volume | 75 μL |
| Sample Conc. | 0.16 mg/ml |
| Run time | 60 min |

In the quantitative HPLC method of Table 3A, the retention time (RT) of colchicine is about 24 minutes and the relative retention times (RRTs) of the common impurities for colchicine are listed in Table 3B:

TABLE 3B

Relative Retention Times (RRTs) of the Common Impurities

| Impurity ID | RRT |
| --- | --- |
| N-deacetyl-N-formyl colchicine - Impurity A | 0.93 |
| Conformational isomer - Impurity B | 0.82 |
| β-Lumicolchicine - Impurity C | 1.76 |
| Colchicoside - Impurity D | 0.18 |
| 3-O-demethyl colchicine - Impurity E | 0.52 |
| 2-O-demethyl colchicine | 0.54 |
| Gamma-Lumicolchicine | 1.37 |

The percentage of individual impurities in the sample solution is calculated as follows:

$$\% \text{ Impurity} = \frac{r_i}{r_s} \times \frac{W_s(\text{mg})}{100 \text{ mL}} \times \frac{6.0 \text{ mL}}{100 \text{ mL}} \times \frac{2.0 \text{ mL}}{100 \text{ mL}} \times P \times \left(\frac{100 - \% \ RS_s - \% \ W_s}{100}\right) \times \frac{200 \text{ mL}}{SW(\text{mg}) \times \left(\frac{100 - \% \ RS_u - \% \ W_u}{100}\right)} \times \frac{100 \%}{RRF}$$

Where:
$r_s$=The area response of the Colchicine peak in the Working Standard Solution.

$r_i$=The area response of the impurity peak in the Sample Solution
P=% Purity of the Colchicine Reference Standard divided by 100%.
SW=Weight of Sample taken for Sample Preparation
$W_s$=Weight of Colchicine in the Stock Standard Solution
RRF=Relative Response Factor for specified and unspecified impurities, 1.0
% $RS_{s/u}$=Percent of Residual Solvents in the Colchicine Standard/Sample
% $W_{s/u}$=% Water in the Colchicine Standard/Sample To date, the impurity colchiceine (Impurity F or 10-O-Demethyl Colchicine "10-DMC") has been typically analyzed by a qualitative colorimetric test described in the Colchicine Official Monograph USP30/NF25 using ferric chloride solution, rather than chromatographically. The standard for acceptable levels of Impurity F has been absence of production of a definite green color in a solution of colchicine.

However, a chromatographic method has been developed for the determination of Impurity F (Colchiceine or 10-O-Demethyl Colchicine "10-DMC"). The chromatographic conditions are as follows:

TABLE 3C

HPLC parameters for Colchiceine determination

| | |
|---|---|
| HPLC System: | HPLC equipped with a pump, auto sampler, variable wavelength detector and a suitable data acquisition system. |
| Column: | Phenomenex Gemini C18 150 mm × 4.6 mm 5 µm, 110 Å |
| Detection: | 245 nm |
| Flow Rate: | About 1.5 mL/min |
| Injection Volume: | 50 µL |
| Temperature: | Column: 10° C. ± 3.5° C. Sample: 5° C. ± 2° C. |
| Needle Rinse Setting: | Double |
| Needle Wash: | Water:Acetonitrile (50:50) |
| Digital Filter Response: | 1.0 |
| Sampling Rate: | 5.0 |
| Resolution: | 1.2 |
| Mobile Phase: | pH 4.5 Buffer Solution:Acetonitrile (75:25) |
| Run Time: | About 7 minutes for Standard About 20 minutes for first Blank and Samples |

The LQL level for 10-DMC in this method is 0.776304 µg/mL. The amount of 10-DMC expressed in percent of Colchicine is calculated as follows:

$$\% \text{ Purity} = \frac{r_i}{r_s} \times \frac{W_s(\text{mg}) \times P}{4000 \text{ mL}} \times \left(\frac{100 - \% RS_s - \% W_s}{100}\right) \times \frac{3.0 \text{ mL}}{100 \text{ mL}} \times \frac{50 \text{ mL}}{W_u(\text{mg}) \times \left(\frac{100 - \% RS_u - \% W_u}{100}\right)} \times \frac{100\%}{RRF}$$

Where:
$r_i$=The peak area response of 10-DMC in the Sample Solution
$r_s$=The peak area response of Colchicine in the Working Standard Solution
$W_s$=The weight of Colchicine in the Stock Standard Preparation
$W_u$=The weight of Colchicine in the Sample Preparation
P=Standard purity factor expressed as labeled (% Purity/100)
% $RS_{s/u}$=Percent of Residual Solvents in the Colchicine Standard/Sample
% $W_{s/u}$=% Water in the Colchicine Standard/Sample
RRF=Relative response factor for 10-DMC=0.88

Ultrapure colchicine may be obtained by various purification methods starting from colchicine-containing botanical extracts, conventional colchicine, or other partially-purified forms of colchicine. In some embodiments, the colchicine is purified from a botanical source. The botanical source can be any capable of providing colchicine, conventional or ultrapure, in quantities suitable for commercial pharmaceutical product manufacture The literature from 1884-1997 on methods of isolation and purification of colchicine from various botanic sources, including for example *C. autumnale* corms or leaves and species of *Gloriosa* has been reviewed. (Kiselev & Yavich, 1991, "METHODS OF ISOLATING ALKALOIDS OF THE COLCHICINE SERIES"; Plenum Publishing Co., English translation of article from Khimiya Prirodnykh Soedinenii, No. 5, pp. 592-600, September-October, 1990). Kiseleve & Yavich also review reports in the literature of impurities detected in colchicine stored for various times, as follows. In an article published in 1944 it was reported that chromatography of colchicine corresponding to the requirements of the USP of that time showed the presence of 5% of impurities and various amount of individual impurities. An article published in 1952 reported that colchicine meeting the requirements of the USP contained about 4% of 3-demethylcolchicine. A 1953 article reported 1.5% of N-formyldeacetylcolchicine isolated and the presence of other accompanying alkaloids in a pharmacopeial sample of colchicine. An investigation of a commercial sample by high-resolution liquid chromatography, published in 1986, reported finding 93.4% of colchicine, 2.9% of N-formyldeactylcholchicine, 1.8% of 17-hydroxycolchicine, and 0.84% of an unknown substance.

Walaszik et al. describes a process of incorporating carbon 14 into *C. autumnale* plants and isolating radioactive colchicine from the radioactive plants (See Walaszik et al., Science (1952) 116:225-227). However, the level of impurities in the isolated radioactive colchicine is not disclosed.

The purification methods disclosed herein produce ultrapure colchicine comprising very low levels of total impurities or individual impurities. In one embodiment, ultrapure colchicine may be obtained from conventional colchicine obtained commercially or produced using solvent extraction of appropriate botanic material as described in more detail below.

In one embodiment, conventional colchicine may be obtained by isolating colchicine from a colchicine chloroform extract. The extract is washed with a mixture of purified water, sodium hydroxide solution, sodium chloride solution and acetic acid. The washed extract is filtered and the resulting concentrate is distilled in two steps, first using methanol, and second using ethyl acetate. The resulting distillate is crystallized. Ethyl acetate can be used to isolate and wash the crystallized colchicine, which is then dried to yield conventional colchicine. The conventional colchicine comprises more than about 3.0% but no more than 5% total impurities.

The conventional colchicine may be used directly in a colchicine composition comprising a pharmaceutically acceptable excipient. It may also be used for further purification to obtain ultrapure forms of colchicine.

In one embodiment of a method of making ultrapure colchicine, the conventional colchicine may be subjected to column chromatography to obtain a purified colchicine concentrate, distilling the purified colchicine concentrate to obtain a colchicine distillate, and crystallizing ultrapure colchicine from the colchicine distillate. The method can further comprise washing the crystallized ultrapure colchicine with a solvent and drying. The ultrapure colchicine comprises no more than about 3.0% of total impurities.

In one embodiment, the column chromatography is carried out using methylene chloride as solvent on a column of neutral alumina. Other solvents or chromatographic media may be used, provided that impurities are removed from the conventional colchicine to the desired level. In another embodiment, distillation of the purified colchicine concentrate is carried out using ethyl acetate. Other organic solvents can be used, provided that impurities are removed from the purified colchicine concentrate. In yet another embodiment, the solvent used to wash the crystallized ultrapure colchicine is ethyl acetate.

In another embodiment, a method of making ultrapure colchicine comprises subjecting colchicine comprising more than about 3.0% total impurities to neutral alumina column chromatography to obtain a colchicine concentrate; distilling the colchicine concentrate with ethyl acetate to obtain a colchicine distillate; crystallizing a purified colchicine from the colchicine distillate in ethyl acetate; washing the purified colchicine with ethyl acetate to obtain a washed purified colchicine; and drying the washed purified colchicine to obtain ultrapure colchicine, wherein the ultrapure colchicine comprises no more than about 3.0% total impurities.

In one embodiment, the ultrapure colchicine obtained in any of the above methods comprises no more than about 2.0% total impurities. In another embodiment, the ultrapure colchicine comprises no more than about 1.5% total impurities. In another embodiment, the ultrapure colchicine comprises no more than about 1.0% total impurities. In another embodiment, the ultrapure colchicine comprises no more than about 0.5% total impurities. In yet another embodiment, the ultrapure colchicine comprises no more than about 0.5% per individual impurity of Impurity A, Impurity B, Impurity C, Impurity D, Impurity E, or Impurity F. In still another embodiment, the ultrapure colchicine comprises no more than about 0.15% per individual impurity of Impurity A, Impurity C, Impurity D, Impurity E, or Impurity F. In another embodiment, the ultrapure colchicine comprises no more than about 1.0% of total unidentified impurities. In yet another embodiment, the ultrapure colchicine comprises no more than about 0.5% of total unidentified impurities. In yet another embodiment, the ultrapure colchicine comprises no more than 1.0% of Impurity B, and no more than 0.1% per individual impurity of any of Impurity A, Impurity C, Impurity D, Impurity E, and Impurity F.

The above methods of making ultrapure colchicine are only examples of suitable methods for its preparation.

The colchicine compositions disclosed herein comprise colchicine and a pharmaceutically acceptable excipient. In one embodiment, the colchicine composition comprises 0.1 wt % to 10 wt % colchicine, specifically 0.1 wt % to 5 wt % colchicine. In one embodiment, the colchicine in the colchicine compositions is ultrapure colchicine. The compositions comprising ultrapure colchicine are stable and provide enhanced safety to patients taking the compositions because the patients are ingesting fewer impurities. In particular, the colchicine compositions contain substantially lower levels of the tumorigenic compound N-deacetyl-N-formyl colchicine.

The pharmaceutically acceptable excipient in the colchicine composition may be a filler (or diluent), a binder, a disintegrant, a lubricant, or a combination comprising two or more of the foregoing excipients.

In one embodiment, the pharmaceutically acceptable excipient comprises a filler. Exemplary fillers may be one or more compounds which are capable of providing compactability and good flow. Exemplary fillers include microcrystalline cellulose, starch, lactose, sucrose, glucose, mannitol, maltodextrin, sorbitol, dextrose, silicic acid, dibasic calcium phosphate, or a combination comprising at least one of the foregoing fillers. Exemplary lactose forms include lactose monohydrate, NF (Fast Flo), lactose spray-dried monohydrate, and lactose anhydrous. Exemplary microcrystalline cellulose (MCC) include, for example, AVICEL® PH101 and AVICEL® PH102, which are commercially available from FMC Biopolymer, Philadelphia, Pa. Exemplary dibasic calcium phosphates include dihydrated and anhydrous dibasic calcium phosphates. In one embodiment, the filler is a combination of microcrystalline cellulose and lactose monohydrate, NF (fast flo).

When present, the amount of the filler in the composition may be about 10 wt % to about 99 wt %, or more specifically, about 30 wt % to about 90 wt %, or even more specifically, about 50 wt % to about 90 wt %, or still more specifically, about 70 wt % to about 85 wt %, based on the total weight of the composition. In one embodiment, the total amount of the filler is about 82 wt %, based on the total weight of the composition In one embodiment, the pharmaceutically acceptable excipient comprises a binder. Binders may be used to impart cohesive qualities to a formulation, for example, a tablet formulation, and thus ensure that the tablet remains intact after compaction. Exemplary binders include starches (for example, Starch 1500® or pregelatinized starch), alignates, gelatin, carboxymethylcellulose, sugars (for example, sucrose, glucose, dextrose, and maltodextrin), polyethylene glycol, waxes, natural and synthetic gums, polyvinylpyrrolidone, and cellulosic polymers (for example, microcrystalline cellulose, hydroxypropyl cellulose, hydroxypropyl methylcellulose, methyl cellulose, and hydroxyethyl cellulose) and combinations comprising one or more of the foregoing binders. In one embodiment, the binder is starch, or more specifically, pregelatinized starch.

When present, the amount of the binder may be about 10 wt % to about 99 wt %, or more specifically, about 10 wt % to about 50 wt %, or even more specifically, about 10 wt % to about 20 wt %, based on the total weight of the composition. In one embodiment, the amount of the binder is about 14 wt %, based on the total weight of the composition.

In another embodiment, the pharmaceutically acceptable excipient comprises a disintegrant. Disintegrants are used to facilitate disintegration or "breakup" of a composition, for example, a tablet, after administration. Exemplary disintegrants include sodium starch glycolate, sodium crosscarmelose (cross-linked carboxy methyl cellulose), crosslinked polyvinylpyrrolidone (PVP-XL), anhydrous calcium hydrogen phosphate, agar-agar, potato or tapioca starch, alginic acid, or a combination comprising one or more of the foregoing disintegrants.

When present, the disintegrant may be present in an amount of about 0.1 to 30 wt %, or more specifically, about 1 to 20 wt %, or even more specifically, about 1 to 10 wt %, based on the total weight of the composition. In one embodiment, the amount of the disintegrant is about 4.5 wt %, based on the total weight of the composition.

In another embodiment, the pharmaceutically acceptable excipient comprises a lubricant. Generally, a lubricant is added just before tableting, and is mixed with the rest of the composition for a minimum period of time to obtain good dispersal. Exemplary lubricants include magnesium stearate, calcium stearate, zinc stearate, stearic acid, talc, glyceryl behenate, polyethylene glycol, polyethylene glycol, polyethylene oxide, sodium lauryl sulfate, magnesium lauryl sulfate, sodium oleate, sodium stearyl fumarate, DL-leucine, colloidal silica, or a combination comprising one or more of the foregoing lubricants. In one embodiment, the lubricant is magnesium stearate, calcium stearate, or zinc stearate.

When present, the lubricant may be present in an amount of about 0.01 wt % to about 10 wt %, or more specifically, about 0.1 wt % to about 5 wt %, or even more specifically, about 0.1 wt % to about 1 wt %, based on the total weight of the composition. In one embodiment, the amount of the lubricant is about 0.6 wt %, based on the total weight of the composition.

If desired, the composition may optionally comprise small amounts of nontoxic auxiliary substances such as wetting or emulsifying agents, or pH buffering agents, for example, sodium acetate, sorbitan monolaurate, triethanolamine sodium acetate, triethanolamine oleate, sodium lauryl sulfate, dioctyl sodium sulfosuccinate, and polyoxyethylene sorbitan fatty acid esters.

In one embodiment, a composition comprises an ultrapure colchicine, wherein the ultrapure colchicine comprises no more than 3.0% of total impurities, a filler, a binder, and a disintegrant.

In another embodiment, a colchicine composition comprises about 0.6 mgA colchicine; about 14 mg pregelatinized starch; about 22 mg microcrystalline cellulose; about 4.3 mg sodium starch glycolate; about 0.6 mg magnesium stearate; and an amount of lactose monohydrate such that the colchicine composition has a total weight of about 100 mg. In one embodiment, the colchicine in the colchicine composition is ultrapure colchicine.

In an embodiment, a colchicine composition comprises colchicine; and a pharmaceutically acceptable excipient; wherein the colchicine composition comprises no more than about 3.5% total impurities, specifically no more than about 3.0% total impurities, more specifically no more than about 2.0% total impurities, or yet more specifically no more than about 1.0% total impurities. In some of these embodiments, specific limitations on the levels of individual impurities are also met by the colchicine composition. In addition to containing no more than a particular maximum level of total impurities, the colchicine composition can comprise not more than about 0.42% Impurity A, Impurity C, Impurity D, Impurity E, or Impurity F, and not more than about 2.0% Impurity B; specifically not more than about 0.2% Impurity A, Impurity C, Impurity D, Impurity E, or Impurity F, and not more than about 1.5% Impurity B; and more specifically not more than about 0.15% Impurity A, Impurity C, Impurity D, Impurity E, or Impurity F, and not more than about 1.1% Impurity B. In one embodiment the colchicine composition comprises no more than 3.5% total impurities, no more than 0.42% Impurity A, and no more than 2.0% Impurity B. The pharmaceutically acceptable excipient can be one or more discussed previously herein.

In one embodiment, a colchicine composition comprises colchicine and a pharmaceutically acceptable excipient; wherein the colchicine composition comprises no more than about 3.5% total impurities. In some embodiments, the colchicine composition comprises ultrapure colchicine and total impurities in the ultrapure colchicine comprise no more than about 3.0%, or specifically no more than about 2.0%, or more specifically no more than about 1.5%, or yet more specifically, no more than about 1.0%. In addition to containing no more than a particular maximum level of total impurities, the ultrapure colchicine in the colchicine composition can comprise not more than about 0.15% Impurity A, Impurity C, Impurity D, Impurity E, or Impurity F, and not more than about 2.0% Impurity B; specifically not more than about 0.10% Impurity A, Impurity C, Impurity D, or Impurity E; not more than about 0.15% Impurity F, and not more than about 1.5% Impurity B. In one embodiment the colchicine composition comprises ultrapure colchicine comprising no more than 0.10% Impurity A, no more than about 0.15% Impurity F, and no more than 2.0% Impurity B. The pharmaceutically acceptable excipient can be one or more discussed previously herein.

In one embodiment, a colchicine composition comprises colchicine; a filler; a binder; and a disintegrant; wherein the colchicine composition comprises no more than about 3.5% total impurities. In some embodiments, the colchicine composition comprises ultrapure colchicine and total impurities in the composition comprise no more than about 3.5%, or specifically no more than about 3.0%, more specifically no more than about 2.0%, or yet more specifically, no more than about 1.0%; with individual impurity levels of not more than about 0.42% for Impurity A, Impurity C, Impurity D, Impurity E, or Impurity F, and not more than about 2.0% for Impurity B. or specifically with individual impurity levels of not more than about 0.10% for Impurity A, Impurity C, Impurity D, Impurity E, or Impurity F, and not more than about 2.0% for Impurity B.

In one embodiment, the percent total impurities in the composition is determined in an HPLC assay as described in Colchicine Official Monograph USP30/NF25 as 100% times a sum of responses of any peaks other than that due to colchicine, eluting within 1.5 times the retention time for colchicine, relative to a sum of responses of all peaks eluting within 1.5 times the retention time for colchicine and the percent of an individual impurity in the composition is determined in an HPLC assay as described in Colchicine Official Monograph USP30/NF25 as 100% times the responses of the impurity peak relative to a sum of responses of all peaks eluting within 1.5 times the retention time for colchicine.

In yet another embodiment, the percent total and/or individual impurities in the composition is determined in an HPLC assay or HPLC assay in accordance with the methods described in Table 2 or Table 3A or 3C.

In one embodiment, any of the colchicine compositions described above is in the form of a tablet. As used herein, the term "tablet" means a compressed pharmaceutical dosage form of any shape or size. The tablets described herein may be obtained from the compositions comprising colchicine and a pharmaceutically acceptable excipient. Any of the colchicine compositions can be in the form of any other dosage form known in the art, specifically, any oral dosage form, for example a capsule.

Either wet or dry granulation of a colchicine composition may be used prior to compressing the composition into tablets, or direct compression can be used.

In one embodiment, wet granulation is used to prepare wet granules comprising colchicine. A granulating liquid is used in wet granulation process. Both aqueous and non-aqueous liquids may be used as the granulating liquid. In one embodiment, the granulating liquid is an aqueous liquid, or more specifically, de-ionized water. In an embodiment, the colchicine is ultrapure colchicine.

The amount of the granulating liquid used may depend on many factors, for example, the type of the granulating liquid, the amount of the granulating liquid used, whether a hygroscopic excipient is used, the nature of the active agent, and the active agent loading. In one embodiment, the amount of the granulating liquid is in the range of about 5 wt % to about 50 wt %, or more specifically, about 10 wt % to about 40 wt %, based on the dry weight of the granulating particles prior to wet granulation.

Wet granulation time is generally about 5 to 60 minutes. In one embodiment, the colchicine particles and suitable excipients are mixed with the granulating liquid for a period of about 5 to about 45 minutes, or more specifically, about 5 to about 35 minutes. For a small scale, the mixing time is about 1 to about 20 minutes, or more specifically, 3 to 10 minutes. Wet granulation is generally performed at temperatures between about 20° C. to about 35° C., or more specifically, at room temperature (about 25° C.).

Any equipment may be used to contact the granulating liquid with the colchicine and the excipients as long as uniform distribution of the granulating liquid is achieved. For example, small-scale production can be achieved by mixing and wetting the ultrapure colchicine and the excipients in mortars or stainless steel bowls, while for larger quantities, V-blenders with intensifier bars, planetary mixers, rotary granulators, high shear granulators, and fluid-bed granulation equipment may be used. In one embodiment, the granulator is a high shear granulator.

In one embodiment, a method of making a colchicine composition comprises wet granulating colchicine with a pharmaceutically acceptable excipient to obtain wet granules, and mixing the granules with a second excipient to obtain a colchicine composition. In one embodiment, the pharmaceutically acceptable excipient comprises a mixture of a filler and a binder. In another embodiment, the mixture of the filler and the binder comprises pregelatinized starch, lactose monohydrate, and microcrystalline cellulose. In another embodiment, de-ionized water is used as the granulating liquid. In some embodiments, the colchicine is ultrapure colchicine. In an embodiment, the second excipient mixed with the granules is a disintegrant. The colchicine compositions can contain about 0.1 wt % to about 10 wt %, or more specifically, about 0.1 wt % to about 1 wt %, of colchicine, based on the total weight of the colchicine composition.

In an embodiment, the method of making a composition comprises wet granulating colchicine with a pharmaceutically acceptable excipient to obtain wet granules, and mixing the granules with a disintegrant to obtain a colchicine composition. In some embodiments, the method further comprises drying the mixture. In another embodiment, the wet granules are dried to obtain dried granules; and then the dried granules are mixed with a disintegrant to obtain the composition. In another embodiment, the dried granules can be milled to obtain milled granules before mixing the milled dried granules with the disintegrant. In one embodiment, greater than 50% of the milled granules pass through a 45 micron sieve or mesh screen. The method can further comprise mixing the colchicine composition with a lubricant to obtain a tableting blend or compressing the tableting blend to obtain a tablet. The method can further comprise coating the tablet.

In one embodiment, a method of making a colchicine composition comprises wet granulating ultrapure colchicine with a pharmaceutically acceptable excipient to obtain wet granules; drying the wet granules to obtain dried granules; milling the dried granules to obtain milled granules; and mixing the milled granules with a disintegrant to obtain the composition. The ultrapure colchicine can comprise no more than about 3.0% total impurities, with no more than about 0.10% Impurity A, no more than about 0.15% Impurity F, and no more than about 2.0% Impurity B.

In another embodiment, a method of making a colchicine tablet comprises wet granulating colchicine with a pharmaceutically acceptable excipient to obtain wet granules; drying the wet granules to obtain dried granules; milling the dried granules to obtain milled granules; mixing the milled granules with a disintegrant to obtain the composition; mixing the composition with a lubricant to obtain a tableting blend; and compressing the tableting blend to obtain a colchicine tablet.

In some embodiments, the wet granules are dried to obtain dried granules before mixing with a second excipient, for example a disintegrant. Wet granules can be dried by any suitable means to remove the granulating liquid and to form dried granules containing colchicine and the pharmaceutically acceptable excipient. The conditions and duration of drying depend on factors such as the liquid used and the weight of the granulating particles. Examples of suitable drying methods include, but are not limited to, tray drying, forced air drying, microwave drying, vacuum drying and fluid bed drying.

The extent of drying may be determined by visual observation and manual manipulation, as is common in the art. The extent of drying may also be determined by sieve analysis, moisture measurements, such as loss on drying (LOD) or other suitable methods. In one embodiment, wet granules are dried until the granules lose less than 5 weight percent (wt %), or more specifically, 3 wt % upon drying at 105° C. based on the total weight of the dried granules prior to drying (or LOD of less than 3 wt %).

After drying, dried granules may be mixed directly with an excipient, for example, a filler, a binder, a disintegrant, or a lubricant, for further processing. Alternatively, dried granules may optionally be subjected to additional processing steps prior to mixing with the excipient. For example, dried granules may be sized to reduce particle size prior to mixing with an excipient. Exemplary sizing operations include milling or sieving. Any suitable equipment for reducing the particle size may be used in the present invention. In one embodiment, the dried granules are milled to obtain milled granules so that at least 50% of the milled granules pass through a 45 micron mesh screen.

Suitable excipients may be added extragranularly and mixed with the granules to form colchicine compositions. As used herein, the term "extragranular" or "extragranularly" means that the referenced material, for example, a suitable excipient, is added or has been added as a dry component after wet granulation. In one embodiment, a disintegrant and a lubricant, in that sequence, are added extragranularly to the granules and mixed to form a blend. The blend may be encapsulated directly into capsule shells, for example, hard gelatin shells, to form capsule formulations. Alternatively, the blend may be compressed into tablets. In some embodiments, the granules are dried granules or milled, dried granules. In some embodiments, the colchicine is ultrapure colchicine.

Mixing can be carried out for a sufficient time to produce homogeneous mixtures or blends. Mixing may be accomplished by blending, stirring, shaking, tumbling, rolling, or by any other method to achieve a homogeneous blend. In some embodiments, the components to be mixed are combined under low shear conditions in a suitable apparatus, such as a V-blender, tote blender, double cone blender or any other apparatus capable of functioning under low shear conditions.

The homogenous mixtures or blends are then compressed using any method suitable in the industry.

The colchicine tablets prepared from the above described methods exhibit acceptable physical characteristics including good friability and hardness. The colchicine tablets disclosed herein have friability in the range of about 0% to 3%, specifically about 0 to 1%, more specifically 0% to 0.5%

The colchicine tablet can be coated. Coating the tablet may be performed by any known process. A coating for the colchicine tablet disclosed herein can be any suitable coating, such as, for example, a functional or a non-functional coating, or multiple functional or non-functional coatings. By "functional coating" is meant to include a coating that modifies the release properties of the total formulation, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

In one embodiment, the tablet is coated with a non-functional coating. The coating can be a white or colored OPADRY® or OPADRY® II (both available from Colorcon, West Point, Pa.), optionally with additional ingredients such as carnauba wax, plasticizers, opacifiers, colorants, and antioxidants. In one embodiment, the coating comprises OPADRY® II and carnauba wax.

In an embodiment, a colchicine composition comprises about 0.6 mgA colchicine; about 12 to about 16 mg pregelatinized starch; about 20 to about 24 mg microcrystalline cellulose; about 3.9 to about 4.7 mg sodium starch glycolate; about 0.5 to about 0.7 mg magnesium stearate; and an amount of lactose monohydrate such that the colchicine dosage form has a total weight of about 100 mg. In some embodiments the colchicine composition comprises about 0.6 mgA colchicine, about 14 mg pregelatinized starch, about 22 mg microcrystalline cellulose, about 4.3 mg sodium starch glycolate, about 0.6 mg magnesium stearate, and an amount of lactose monohydrate such that the colchicine dosage form has a total weight of about 100 mg. The colchicine composition can be in the form of a tablet. In some embodiments the tableted composition further comprises a coating comprising Opadry® II and carnauba wax. In an embodiment, the colchicine is ultrapure colchicine.

In one embodiment, a colchicine composition comprising ultrapure colchicine is formulated into an immediate-release formulation. By "immediate-release" is meant a conventional or non-modified release in which greater than or equal to about 75% of the active agent is released within two hours of administration, specifically within one hour of administration.

Active agent release from a pharmaceutical formulation can be analyzed in various ways. One exemplary test is in vitro dissolution. A dissolution profile is a plot of the cumulative amount of active agent released from a formulation as a function of time. A dissolution profile can be measured utilizing the Drug Release Test <724>, which incorporates standard test USP 26 (Test <711>). A profile is characterized by the test conditions selected such as, for example, apparatus type, shaft speed, temperature, volume, and pH of the dissolution medium. More than one dissolution profile may be measured. For example, a first dissolution profile can be measured at a pH level approximating that of the stomach, and a second dissolution profile can be measured at a pH level approximating that of one point in the intestine or several pH levels approximating multiple points in the intestine.

In one embodiment, the immediate-release colchicine composition exhibits a dissolution profile such that at ten minutes after combining the composition with 500 ml of purified water at 37° C.±0.5° C. according to USP 28 <711> Apparatus 1 (basket), 100 rpm speed, about 90 to about 100 wt. % of the total amount of active agent is released; specifically at 30 minutes after combining the composition with the dissolution medium, about 95 to about 100 wt. % of the total amount of colchicine is released; and more specifically at one hour after combining the composition with the dissolution medium, about 98 to about 100 wt. % of the total amount of colchicine is released.

Potency, or the amount of active colchicine present in a batch of colchicine, can be determined as described in Colchicine Official Monograph USP 30/NF 25 by comparing an assay sample to a colchicine reference standard (e.g., USP Colchicine RS) sample in the chromatographic assay described in Colchicine Official Monograph USP30/NF25 The quantity of active colchicine in the assay sample, in mg, of $C_{22}H_{25}NO_6$ is calculated by the formula: $10C(r_U/r_S)$, in which C is the concentration, in μg per mL, of the colchicine reference standard sample; and $r_U$ and $r_S$ are the colchicine peak responses obtained from the assay sample and the colchicine reference standard sample, respectively.

In another embodiment, potency of a batch of colchicine can be determined using the HPLC Potency assay described in the table below by comparing an assay sample to a colchicine reference standard.

| | HPLC Potency Assay B |
|---|---|
| Mobile phase | 50 mM Potassium Phosphate Buffer:methanl (45:55), pH 5.5 ± 0.05 |
| Column | Phenomenex Luna C8(2), 4.6 mm × 25 cm, 5 μm |
| Flow rate | 1.0 mL/min |
| Column Temperature | Ambient |
| Detection | 254 nm |
| Injection volume | 20 uL |
| Sample Conc. | 0.120 mg/ml |
| Run time | 15 min |

The quantity, in percentage, of $C_{22}H_{25}NO_6$ (active colchicine), on an anhydrous, solvent free basis, in the colchicine assay sample is calculated by the formula:

$$\% \text{ Purity} = \frac{r_u}{r_s} \times \frac{W_s(\text{mg}) \times P \times \left(\frac{100 - M_s - S_s}{100}\right)}{500 \text{ ml}} \times$$

$$\frac{PV(\text{ml})}{VF(\text{ml})} \times \frac{VF_1(\text{ml})}{SW(\text{mg}) \times \left(\frac{100 - M_u - S_u}{100}\right)} \times \frac{VF_2(\text{ml})}{PV_1(\text{ml})} \times 100$$

Where:
  $r_u$=The peak area of colchicine in the working sample solution
  $r_s$=The peak area of colchicine in the working standard solution
  $W_s$=The weight of colchicine in the standard preparation
  P=Standard purity factor expressed as labeled % Purity
  $M_s$=Moisture factor in standard expressed as % Moisture
  $S_s$=Solvent factor in standard expressed as % Solvent
  PV=Pipet volume used for the working standard solution
  VF=Volumetric flask used for the working standard solution
  SW=Sample weight in the stock sample solution
  $VF_1$=Volumentric flask used for the stock sample solution
  $M_u$=Moisture factor in sample expressed as % Moisture
  $S_u$=Solvent factor in sample expressed as % Solvent
  $VF_2$=Volumentric flask used for the working sample solution
  $PV_1$=Pipet volume used for the working sample solution.

Alternatively, potency of a batch of colchicine can be determined by comparing an assay sample to a colchicine reference standard in yet another HPLC assay as follows:

| HPLC Potency Assay C | |
|---|---|
| HPLC System: | HPLC equipped with a pump, autosampler, variable wavelength detector and a suitable data acquisition system |
| Column Information: | Phenomenex Gemini C18 150 × 4.6 mm 5 μm 110 Å |
| Detection: | 245 nm |
| Flow Rate: | 1.5 mL/minute |
| Injection Volume: | 20 μL |
| Column Temperature: | 30° C. ± 3° C. |
| Needle Rinse Setting: | Double |
| Sampling Rate: | 2.0 |
| Resolution: | 1.2 |
| Filter Response: | 1.0 |
| Digital Filter: | Enabled |
| Needle Wash/Seal Wash: | Methanol:Water (50:50) |
| Run Time: | About 15 minutes |
| Mobile Phase: | pH 6.0 Buffer Solution (50 mM of Potassium phosphate and 4 mM of EDTA):Methanol (60:40) |
| Diluent: | Water:Methanol (75:25) |

The percent purity of Colchicine ($C_{22}H_{25}NO_6$), on an anhydrous, solvent-free basis, is calculated as follows:

$$\% \text{ Assay} = \frac{r_u}{r_s} \times \frac{W_s(\text{mg}) \times P}{50 \text{ mL}} \times \left(\frac{100 - \% \text{ } RS_s - \% \text{ } W_s}{100}\right) \times$$

$$\frac{5.0 \text{ mL}}{100 \text{ mL}} \times \frac{500 \text{ mL}}{W_u(\text{mg}) \times \left(\frac{100 - \% \text{ } RS_u - \% \text{ } W_u}{100}\right)} \times 100\%$$

Where:
$r_u$=The peak area response of Colchicine in the Sample Solution.
$r_s$=The peak area response of Colchicine in the Working Standard Solution.
$W_s$=The weight of Colchicine in the Stock Standard Preparation.
$W_u$=The weight of Colchicine in the Sample Preparation.
P=Standard purity factor expressed as labeled (% Purity/100).
% $RS_{s/u}$=Percent of Residual Solvents in the Colchicine Standard/Sample.
% $W_{s/u}$=% Water in the Colchicine Standard/Sample.

Disclosed herein are also methods of treatment and dosing regimens.

The compositions comprising ultrapure colchicine disclosed herein may be used to treat or prevent a patient's condition such as acute gouty arthritis, chronic gouty arthritis, acute pericarditis, asthma, Behçet's disease, cancer, chronic gout (prophylaxis), pseudogout cystic disease comprising polycystic kidney disease or cystic fibrosis, demyelinating disease of central or peripheral origin, Dupuytren's contracture, Familial Mediterranean fever, glaucoma, idiopathic pulmonary fibrosis, idiopathic thrombocytopenic purpura, inflammatory disorder comprising rheumatoid arthritis, lentiviral infection, multiple sclerosis, postpericardiotomy syndrome, primary amyloidosis, primary biliary cirrhosis, proliferative vitreoretinopathy, pyoderma gangrenosum, recurrent pericarditis, or a condition in need of enhanced bone formation or bone mineral density.

The traditional dose of colchicine used to treat or prevent an attack of acute gouty arthritis has been about 1.0 to about 1.2 mgA of colchicine, for example, two tablets each comprising about 0.6 mgA colchicine. This dose may be followed by one unit of the composition every hour, or two units every two hours, until pain is relieved or until diarrhea ensues ("diarrheal dose"). After the initial dose, it is sometimes sufficient to take about 0.6 mgA colchicine every two or three hours. The dosing should be stopped if there is gastrointestinal discomfort or diarrhea. (Opiates may be needed to control diarrhea.) In subsequent attacks, the patient should be able to judge his medication requirement accurately enough to stop short of his diarrheal dose. The total amount of colchicine needed to control pain and inflammation during an attack has been believed to be in the range from about 4 mgA to about 8 mgA. An interval of three days between colchicine courses is advised in order to minimize the possibility of cumulative toxicity.

In one embodiment, a method of treating acute gouty arthritis comprises administering two colchicine dosage forms each comprising about 0.6 mgA colchicine at the onset of the acute gout attack, followed by one dosage form every hour for m hours, wherein the value of m is 1 to 8. In one embodiment, the value of m is 1 to 6. In another embodiment, the value of m is 1 (total of 3 tablets). In yet another embodiment, the value of m is 6 (total of 8 tablets). The colchicine in the dosage form can be ultrapure colchicine. The dosage form can be any oral dosage form, specifically a tablet.

In another embodiment, a method of treating Familial Mediterranean Fever comprises administering ½ dosage form to four dosage forms daily, each dosage form comprising about 0.6 mgA colchicine (total of about 0.3 to about 2.4 mgA colchicine daily). In another embodiment, a method of prophylactically treating chronic gout comprises administering one-half dosage form, one dosage form, two dosage forms, or three dosage forms, each dosage form comprising about 0.6 mgA of colchicine, daily. In another embodiment, a method of treating Behçet's disease comprises administering one dosage form comprising about 0.6 mgA of colchicine twice daily (total of 2 dosage forms). The colchicine in the dosage form can be ultrapure colchicine. The dosage form can be any oral dosage form, specifically a tablet.

In one embodiment, a method of treating patients with some but not all of the symptoms of acute gout, chronic gout (prophylaxis), or pseudogout, where the patients are not clinically or informally diagnosed with one of these diseases, comprises administering one or more of the dosage forms comprising about 0.6 mgA of colchicine. The colchicine in the dosage form can be ultrapure colchicine.

The invention should not be considered limited to these particular conditions for combining the components and it will be understood, based on this disclosure that the advantageous properties can be achieved through other conditions provided the components retain their basic properties and substantial homogeneity of the blended formulation components of the formulation is otherwise achieved without any significant segregation.

The following examples further illustrate the invention but should not be construed as in any way limiting its scope. In particular, the processing conditions are merely exemplary and can be readily varied by one of ordinary skill in the art.

EXAMPLES

Example 1

Exemplary Ultrapure Colchicine

As discussed above, ultrapure colchicine with reduced levels of individual and total impurities was desired by the inventors for formulation into a new dosage form in order to minimize potential adverse reactions from the impurities in patients taking the dosage form and to reduce the expense of qualification testing during the approval process for marketing the new dosage form. Batches of conventional colchicine were previously obtained from Sanmar Specialty Chemicals Limited (Berigari, India). Conventional colchicine can be further purified to form ultrapure colchicine meeting the following impurity specifications:

TABLE 4

Purity Specifications for an exemplary batch of Ultrapure Colchicine

| Impurity, Common name | Impurity | NMT % |
|---|---|---|
| N-deacetyl-N-formyl colchicine | A | 0.10 |
| Conformational isomer | B | 1.0 |
| β-Lumicolchicine | C | 0.10 |
| Colchicoside | D | 0.10 |
| 3-O-demethyl colchicine | E | 0.10 |
| Total Impurities | | 2.0 |

Ultrapure colchicine was prepared to meet the purity specifications in Table 4 as described below.

First, conventional colchicine was obtained from a colchicine chloroform extract. The extract was washed with a mixture of purified water, sodium hydroxide solution, sodium chloride solution and acetic acid. The washed extract was filtered and the resulting concentrate was distilled in two steps, first using methanol, and second using ethyl acetate. The resulting distillate was crystallized. Ethyl acetate was used to isolate and wash the crystallized colchicine, which was then dried, resulting in the conventional colchicine. This process is also referred to herein as the "old process".

Second, the conventional colchicine was then subjected to column chromatography on neutral alumina using methylene chloride as solvent. The resulting concentrate was distilled using ethyl acetate, crystallized, isolated and washed using ethyl acetate, and dried, resulting in ultrapure colchicine. This method of generating conventional colchicine, followed by the additional chromatography purification step is also referred to herein as the "new process".

The impurity levels of the lot of ultrapure colchicine and two lots of conventional colchicine were analyzed using the USP30/NF25 Colchicine Official Monograph HPLC method ("USP method") described in Table 2 above. The impurity levels are shown in Table 5.

TABLE 5

| | Impurity Level, % | | | |
|---|---|---|---|---|
| Colchicine Lot | N-Deacetyl-N-formyl colchicine - Impurity A | Conformational Isomer - Impurity B | Total Unidentified Impurities | Total Impurities |
| Ultrapure (RD0600164) | ND* | 0.5 | ND* | 0.5 |
| Conventional-1 (RD060075) | 2.1 | 0.6 | ND* | 2.7 |
| Conventional 2 (RD060055) | 2.2 | 0.6 | ND* | 2.8 |

*ND—None detected.

Table 5 shows that ultrapure colchicine has fewer impurities than each of the conventional colchicine lots. Total impurities of the Ultrapure Lot using the USP method were about 0.5%. On the other hand, total impurities of conventional Lots #1 and 2 were about 2.7% and 2.6%, respectively.

Determined impurity levels may differ depending on the test method used. Table 5B contrasts the determined levels of the conformational isomer, Impurity A (N-deacetyl-N-formyl colchicine), and total impurities for the three colchicine lots using the three methods described in Table 2. The three methods show a maximum absolute variability in the percent determined of 0.8% for N-deacetyl-N-formyl colchicine, of 0.5% for conformational isomer, and 0.7% for total impurities.

TABLE 5B

Levels of impurities in colchicine lots determined using methods of Table 2.

| | | Conformational Isomer | | | N-deacetyl-N-formyl colchicine | | | Total Impurities | | |
|---|---|---|---|---|---|---|---|---|---|---|
| Lot name (Lot #) | Purification Process | UPLC Method | HPLC Method | USP Method | UPLC Method | HPLC Method | USP Method | UPLC Method | HPLC Method | USP Method |
| Conventional-1 (RD060055) | Old | 0.9 | 0.8 | 0.6 | 3.0 | 2.5 | 2.2 | | 3.5 | 2.8 |
| Conventional 2 (RD060075) | Old | 0.9 | 0.8 | 0.6 | 2.7 | 2.3 | 2.1 | | 3.2 | 2.7 |
| Ultrapure (RD0600164) | New | 0.9 | 1.0 | 0.5 | ND* | ND | ND | | 1.1 | 0.5 |

*ND, none detected.

Regardless of the testing method used for measuring these impurity levels, the impurity levels for ultrapure colchicine manufactured using the new process remains below the specifications set forth in Table 4.

The ultrapure colchicine of the present invention was prepared to meet the organic volatile impurity specifications ("residual solvents") in Table 6 as described below. The residual solvents are determined using USP <467> test method. In addition to the known and existing solvents, specifications were also set for residual solvent peaks that were seen in HPLC assay testing as described in Tables 2, 3A, or 3C, which solvents are not expected or previously existing for the residual solvent test methods for colchicine or were not identifiable.

TABLE 6

Specifications for Organic Volatile Impurities

| Organic volatile | NMT |
|---|---|
| Chloroform | 100 ppm |
| Methanol | 3000 ppm |
| Methylene Chloride | 600 ppm |
| Ethanol | 5000 ppm |
| Ethyl Acetate | 6.0% |
| Ethyl Propionate | 5000 ppm |
| Propyl Acetate | 5000 ppm |
| Others | 500 ppm each |

This final tableting blend was compressed into core tablets. These core tablets were film-coated with OPADRY® II purple and carnauba wax. The composition of the ultrapure colchicine tablets is shown in Table 7.

TABLE 7

| Ingredient | Amount Per Tablet, mg |
|---|---|
| Ultrapure Colchicine | 0.6[1] |
| Pregelatinized starch, NF (Starch 1500) | 14.0 |
| Lactose Monohydrate, NF (Fast Flo) | Varies[2] |
| Microcrystalline Cellulose, NF (Avicel PH101) | 21.6 |
| Sodium Starch Glycolate, NF (GLYCOLYS) | 4.3 |
| Magnesium Stearate, NF | 0.6 |
| Total core tablet | 100 |
| OPADRY II Purple (#40L10039) | 4.0 |
| Carnauba Wax | 0.01 |

[1]Colchicine amount is shown in units of mgA, adjusted for purity of the lot of colchicine.
[2]Amount adjusted, depending on the actual amount of the colchicine lot added, to maintain an overall core tablet weight of 100 mg.

As a comparison, the lot of conventional colchicine designated in Example 1 as "conventional-2" was substituted in place of ultrapure colchicine in the same tablet formulation shown in Table 7. The same process of making the tablets as described above was used.

The impurities in the tablet comprising the ultrapure colchicine and that comprising the conventional colchicine were analyzed using the HPLC method described in Table 2 above. The impurity levels of both colchicine tablets are shown in Table 8.

TABLE 8

| | | | Impurity Content, % | | | |
|---|---|---|---|---|---|---|
| Colchicine Product Lot | Colchicine Lot | Process | N-Deacetyl-N-formyl colchicine (Impurity A) | Conformation Isomer (Impurity B) | Total Unknown Impurities | Total Impurities |
| A | Ultrapure | New | ND* | 1.1 | 0.1 | 1.2 |
| B | Conventional-2 | Old | 2.3 | 1.2 | ND* | 3.6 |

*ND—None detected.

Example 2

Stable Tablets Comprising Ultrapure Colchicine

Stable colchicine compositions comprising the ultrapure colchicine described in Example 1 were manufactured using the following process. Ultrapure colchicine as described in Example 1 was dissolved in purified water. Pregelatinized starch (Starch® 1500), lactose monohydrate, NF (Fast Flo), and microcrystalline cellulose, NF (Avicel PH101) were placed in a 150-liter high shear granulator and mixed. The aqueous ultrapure colchicine solution was added to the granulator while mixing. The wet granules were dried in an oven at 50° C. until the loss on drying of the material was less than 3 wt %. The dried granules were milled through a Fitzmill equipped with a 1β screen.

The milled granules were charged into a 5 cubic foot Gemco Double Cone Blender and blended with screened sodium starch glycolate, NF (GLYCOLYS®). Then, screened magnesium stearate, NF was added to the blender. Blending was continued and a final tableting blend was made.

It can be seen from Table 8 that the tablet comprising the ultrapure colchicine has less total impurities than that comprising the conventional colchicine.

The colchicine composition comprising ultrapure colchicine at 6 month stability time points under conditions of 25° C./60% relative humidity and 40° C./60% relative humidity exhibits impurity content ranges of Not Detected to about 0.1% for Impurity A, less than about 1.0% for total unknown impurities compared to a colchicine composition comprising conventional colchicine which exhibits impurity content of greater than about 1.5 for Impurity A and greater than about 2.0% for total unknown impurities when tested under the same conditions.

Table 9 below provides data on impurity levels and stability of impurity levels of colchicine composition batches manufactured using ultrapure and conventional colchicine, and impurity levels for two lots of commercially available COL-PROBENECID® tablets (Watson Laboratories), an FDA-approved combination dosage form comprising colchicine and probenicid.

TABLE 9

| Material | Lot | Colchicine purification Process | Conditions of Stability Study | Conformational Isomer UPLC Method | Conformational Isomer HPLC Method | N-Deacetyl peak UPLC Method | N-Deacetyl peak HPLC Method |
| --- | --- | --- | --- | --- | --- | --- | --- |
| COL-PROBENECID ® (Probenecid/Colchicine) Tablets† | L6C0395 | N/A | N/A | 0.8 | — | 2.2 | — |
| | L6M1440 | N/A | N/A | 0.8 | — | 2.5 | — |
| Colchicine Product Lot | B | Old process | room temp, at release | 0.9 | 1.2 | 2.8 | 2.3 |
| | | | 12 mo 25 C./60% RH | 0.9 | 0.9 | 2.7 | 2.6 |
| | A | New process | room temp, at release | 1.0 | 1.2 | ND | ND |
| | | | 6 mo 25 C./60% RH | 1.0 | 0.8 | ND | ND |
| | | | 6 mo 40 C./75% RH | 1.0 | 1.1 | ND | ND |
| | C | New process | room temp, at release | 1.0 | 1.1 | ND | ND |
| | | | 6 mo 25 C./60% RH | 0.9 | 0.9 | ND | ND |
| | | | 6 mo 40 C./75% RH | 1.0 | 1.1 | ND | ND |
| | D | New process | room temp, at release | 1.0 | 1.1 | ND | ND |
| | | | 6 mo 25 C./60% RH | 1.0 | 1.0 | ND | ND |
| | | | 6 mo 40 C./75% RH | 0.9 | 1.1 | ND | ND |

—, not analyzed;
†Commercially available;
N/A, not applicable;
ND, none detected.

For comparison, several lots of an FDA-approved colchicine-probenecid combination dosage form and various unapproved commercial colchicine dosage forms were tested for levels of impurities using the HPLC method of Table 2. Results are shown in the tables below.

Impurities in FDA-Approved Colchicine/Probenecid Combination Product

| | Watson Laboratories Colchicine/Probenecid Tablets | | | |
| --- | --- | --- | --- | --- |
| Impurity | L7G1085 | L7G1085 | L7G1087 | L7E0808 |
| Conformational Isomer | 1.0% | 1.0% | 0.8% | 1.0% |
| N-deacetyl-N-formyl colchicine | 2.0% | 2.0% | 1.5% | 2.0% |
| Largest Unknown | 0.1% | 0.1% | 0.1% | 0.1% |
| Total Impurities | 3.1% | 3.1% | 2.4% | 3.2% |

Impurities in Unapproved Colchicine Products

| | West-Ward | | | Vision | | |
| --- | --- | --- | --- | --- | --- | --- |
| Impurity | 62303A* | 63842A | 63843A | C07003 | C07049 | C07058 |
| Exp Date | Jan-2009 | May-2011 | May-2011 | Jan-2009 | Aug-2009 | Sep-2009 |
| Conformational Isomer | 1.1/0.9% | 0.9% | 0.9% | 1.1/0.8% | 0.9% | 0.9% |
| N-deacetyl-N-formyl colchicine | 2.5/2.6% | 2.0% | 1.8% | 1.3/1.3% | 2.7% | 2.6% |
| Largest Unknown | 1.7/1.6% | 0.5% | 0.3% | 0.1/0.1% | 0.1% | 0.3% |
| Total Impurities | 5.3/5.3% | 3.5% | 3.1% | 2.5/2.3% | 3.8% | 4.0% |

| | Qualitest | | | Akyma |
| --- | --- | --- | --- | --- |
| Impurity | T105G07A | T107G07A | T108G07A | 3A5246004* |
| Exp Date | Jul-2010 | Jul-2010 | Aug-2010 | Jan-2008 |
| Conformational Isomer | 1.0% | 0.9% | 0.9% | 1.1/0.9% |
| N-deacetyl-N-formyl colchicine | %1.4 | 1.3% | 1.3% | 1.4/1.5% |
| Largest Unknown | 0.3% | 0.2% | 0.2% | 0.2/0.1% |
| Total Impurities | 2.7% | 2.7% | 2.6% | 2.9/2.5% |

*Values from two separate analyses reported

Summary of Impurities in Marketed Colchicine Products with
Batches of colchicine tablets using ultrapure colchicine

| Impurity | Marketed Colchicine Products | | Product Lots with Ultrapure Colchicine |
| --- | --- | --- | --- |
| | Minimum | Maximum | Maximum |
| Conformational Isomer | 0.8% | 1.1% | 1.1% |
| N-deacetyl-N-formyl colchicine | 1.3% | 2.7% | ND |
| Largest Unknown | 0.1% | 1.7% | 0.3% |
| Total Impurities | 2.4% | 5.3% | 1.4% |

ND = none detected

The total impurities found in ultrapure colchicine and colchicine products comprising ultrapure colchicine are significantly lower compared to the approved and unapproved, marketed colchicine products. In addition, the maximum total impurities value observed by testing 14 approved or unapproved marketed products was 5.3%; while the maximum value seen to date in inventive ultrapure colchicine product batches was 1.4%. This represents a 75% reduction in total impurities.

Of particular significance, the level of the known impurity, N-deacetyl-N-formyl-colchicine (Impurity A, also known as Gloriosine) has been reduced from levels exceeding 2% to levels to undetectable levels that comply with the ICH Q3A (R2) qualification threshold of 0.15% for an active agent. Gloriosine is tumorigenic and has been studied as an anticancer agent. Purification of conventional colchicine to obtain ultrapure colchicine has effectively reduced all individual impurity levels in the colchicine to substantially reduce exposure of patients to this tumorigenic impurity.

Example 3

Therapeutic Effects of Ultrapure Colchicine Formulation

The therapeutic effect of the ultrapure colchicine formulation containing 0.6 mgA of colchicine obtained in Example 2 is evaluated in a clinical study that is a multicenter, randomized, double-blind, placebo-controlled, parallel group, 1-week, dose comparison study designed to evaluate the efficacy of ultrapure colchicine in treating an acute gout attack (acute gouty arthritic attack) in patients with acute gout. A sufficient number of patients are screened to enroll and randomize 300 patients (100 patients per treatment group) who meet the criteria of the American College of Rheumatology (ACR) for acute arthritis of gout. The primary objective of the study is to demonstrate the efficacy of colchicine in an acute gout attack (gouty flare) based on pain reduction after 24 hours as a measure of response. Secondary objectives of the study are to compare low-dose and standard-dose dosing regimens of colchicine with respect to pain, time to response and complete pain relief, interference with sleep, and signs and symptoms of inflammation and to determine the safety of colchicine when administered in the two different dosing regimens.

Description of Study

The study will consist of three distinct phases and the number of visits to the study clinic will vary depending on conditions pertaining to an individual patient's acute gout flare experienced in the study as described below. The Pre-Flare Phase will consist of up to two visits to the study clinic (with additional interim visits for clinical laboratory testing every 3 months until acute gout flare onset): Visit 1 (Screening) and Visit 2 (Randomization). The Flare Phase will not include a visit to the study clinic. The Post-Flare Phase will consist of up to three visits to the study clinic: Visit 3 (as soon as possible [ASAP] up to 48 hours post-flare onset; if a patient cannot complete Visit 3 in the first 48 hours post-flare onset, Visit 3 will be waived and the patient should return to the clinic for Visit 4), Visit 4 (>48 to 96 hours post-flare onset in patients who took at least one dose of study drug and in patients who did not qualify for treatment with study drug during the Flare Phase but did not complete Visit 3), and Visit 5 (7 days post-flare onset to be conducted in patients who took at least one dose of study drug and whose acute gout flare was still ongoing at Visit 4). For those patients in whom the acute gout flare is not resolved at Visit 5 (based on the judgment of the Investigator) or in whom there is an unresolved AE or clinically significant treatment-emergent laboratory abnormality, there will be one additional follow-up visit 14 days post-flare onset (Visit 6).

When a patient develops an acute gout flare, the patient will call the trained personnel at the Gout Flare Call Center (available 24 hours/day throughout the duration of the study). The patient will be queried regarding any changes in his/her medical health and concomitant medication use since the time of randomization. In order to establish if the patient's acute gout flare will be eligible for treatment with study drug, a standardized questionnaire will be used to document that the patient has all of the following signs/symptoms of the affected joint(s): swelling, erythema, marked tenderness, and pain. In addition, a patient must have at least one of the following: rapid onset of maximum pain within the prior 4 to 12 hours, decreased range of motion in the joint, warmth, or other symptom similar to a prior gout flare. Patients will be asked to rate the pain severity for each joint affected by the acute gout flare by using a study diary. Patients must have at least one joint affected by an acute gout flare with a pain assessment of $\geq 4$ on the PI-NRS at the onset of the acute gout flare during the Flare Phase prior to taking study drug. If signs and symptoms of an acute gout flare are confirmed and the gout flare is considered eligible for treatment with study drug, the patient will also be instructed to begin taking study drug and to continue completing the patient diary. Patients will be instructed to stop taking study drug and to call the investigational site if at any time they experience a severe gastrointestinal event while taking study drug. The Gout Flare Call Center will call the patient in 24 hours from the onset of the acute gout flare to ensure that the patient has completed the patient diary, including assessments for pain at 24 hours.

In the event that the Gout Flare Call Center determines that the patient does not qualify for treatment with study drug, the patient may be asked to call back in 1 hour for re-assessment. Patients who do not qualify for treatment with study drug may seek alternative therapy without prejudice to further study participation should another acute gout flare occur.

The Gout Flare Call Center will contact patients on a monthly basis beginning 1 month after randomization to study drug. These contacts will continue until the patient has an acute gout flare or study completion, whichever occurs first. The purpose of these contacts is to re-educate patients about study participation.

Post-Flare Phase:

Visit 3: After developing an acute gout flare, whether eligible for treatment with study drug or not, all patients will return to the clinic as soon as possible after acute gout flare onset for clinical assessments. If a patient cannot complete Visit 3 in the first 48 hours post-flare onset, Visit 3 will be waived and the patient should return to the clinic for Visit 4. For patients whose acute gout flare was deemed eligible for treatment with study drug and at least one dose of study drug was taken, Investigators will examine the patient and complete clinical assessments, patient diaries will be collected, the patient will be queried for concomitant medication use and Adverse Events (AEs), and the study drug blister pack will be collected. For patients whose acute gout flare was deemed not eligible for treatment with study drug by the Gout Flare Call Center, continued eligibility for the study will be confirmed by the Investigator based on review of the inclusion and exclusion criteria as well as the responses to the standardized questionnaire and examination of the patient. Patient diaries will be collected and patients will be queried for concomitant medication use and AEs.

Visit 4: The second Post-Flare Phase visit is to be conducted >48 to 96 hours following acute gout flare onset. It will take place in patients who took at least one dose of study drug and also in those patients who did not qualify for treatment with study drug during the Flare Phase but did not complete Visit 3. For patients whose acute gout flare was deemed eligible for treatment with study drug and at least one dose of study drug was taken, Investigators will examine the patient and complete clinical assessments, patient diaries will be collected, patients will be queried for concomitant medication use and AEs, and the study drug blister pack will be collected (if not previously collected). Patients who took at least one dose of study drug and whose acute gout flare is still ongoing at Visit 4 will return to the clinic for a final visit (Visit 5) 7 days post-flare onset; however, if their acute gout flare is resolved at Visit 4, final study assessments, including collection of samples for laboratory safety and a complete physical examination, will be performed at Visit 4. For patients whose acute gout flare was deemed not eligible for treatment with study drug by the Gout Flare Call Center who did not have a Visit 3, continued eligibility for the study will be confirmed by the Investigator based on review of the inclusion and exclusion criteria as well as the responses to the standardized questionnaire and examination of the patient. Patient diaries will be collected and patients will be queried for concomitant medication use and AEs.

Visit 5/Early Termination: The final visit for the study will take place 7 days after the acute gout flare onset in patients who took at least one dose of study drug and whose acute gout flare was still ongoing at Visit 4. Patients will be examined and clinical assessments will be made. A complete physical examination will be conducted. Samples for clinical laboratory testing will be collected. Patient diaries will be collected and patients will be queried for concomitant medication use and AEs. The study drug blister pack will be collected (if not previously collected).

Visit 6/Follow-up: For those patients in whom the acute gout flare is not resolved at Visit 5 (based on the judgment of the Investigator) or in whom there is an unresolved AE or clinically significant treatment-emergent laboratory abnormality, there will be one additional follow-up visit 14 days post-flare onset (Visit 6).

For inclusion in the study, a patient must be 18 years of age or older, must present with a confirmed diagnosis of gout consistent with the criteria of the ACR, and must have experienced $\geq 2$ acute gouty arthritic attacks in the 12 months prior to randomization. Patients on urate-lowering therapy must be on a stable dose and schedule with no changes in therapy for 4 weeks prior to randomization and expected to remain on a stable regimen during study participation.

Patients with acute polyarticular gout (>4 joints); taking colchicine routinely; with a known hypersensitivity to colchicine; with a history of myocardial infarction, unstable angina, cerebrovascular events, or coronary artery bypass grafting; with active myeloid leukemia, obstructive gastrointestinal cancer, or metastatic cancer; with chronic renal dysfunction, with chronic hepatic dysfunction are excluded from the study. Patients using systemic corticosteroid, cyclosporine, adalimumab, etanercept, infliximab, anakinra, abatacept, mycophenolate, azathioprine, or chronic use of non-steroidal anti-inflammatory drugs (NSAIDs), acetaminophen, tramadol, and other analgesics such as opiates at screening are also be excluded.

The three treatment groups in this study are two ultrapure colchicine tablets (1.2 mgA) administered at the onset of an acute gout attack followed by one tablet (0.6 mgA) after one hour and one placebo tablet every hour thereafter for 5 hours (the "low" dose regimen); two ultrapure colchicine tablets (1.2 mgA) administered at the onset of an acute gout attack followed by one tablet (0.6 mgA) every hour for six (6) hours (the "standard" dose regimen); or two placebo tablets at the onset of an acute gout attack followed by one placebo capsule every hour thereafter for 6 hours (the "placebo" regimen).

Efficacy assessment will be made based on patient and Investigator inputs. Patients will record pain severity and sleep interference on a study diary. The severity of pain for each joint affected by the acute gouty arthritic attack will be rated on an 11-point pain intensity numerical rating scale (PI-NRS) that ranges from 0 ("no pain") to 10 ("worst possible pain"). Recordings are to be made prior to each dose of study drug, i.e., pre-treatment with study drug and for the first 8 hours following start of treatment, and every 8 hours thereafter (while awake) until symptoms disappear or 72 hours have passed since the first dose of study drug was taken, whichever occurs first. The patient's pain assessment of each affected joint as reported by the patient at pre-treatment with study drug and at 24 hours post-start of study drug will be documented by a central Study Center to be used in the event the patient fails to provide data on his/her study diary for either of these two key time points. In the morning upon awakening, the patient is to rate sleep interference due to the acute gout flare in the study diary on an 11-point scale that ranges from 0 ("pain did not interfere with sleep") to 10 ("pain completely interfered; patient was unable to sleep"). Investigators will provide clinical assessments in the clinic at all Post-Flare Phase study visits, and at medically necessary intervening visits. For these assessments, each of the patient's joints affected by the acute gouty arthritic attack will be examined and signs and symptoms of inflammation will be rated (erythema [absent, present, or not assessable], swelling [0, "none" to 3, "severe"], and tenderness to touch [0, "none" to 3, "severe"]). At the final clinic visit, the Investigator will also provide a global assessment of response to treatment ranging from 0 ("excellent") to 4 ("none").

The primary efficacy variable is response to treatment in the target joint, based on patient self-assessment of pain at 24 hours post-dose. The target joint is identified during data analysis as that joint affected by the acute gout flare with the highest baseline pain score on the patient diary. Ties among maximum joint scores for an individual are resolved by random selection. A responder is one who provides both a pre-treatment and valid 24-hour pain score and achieves a $\geq 50\%$ reduction in pain score at the 24-hour post-dose assessment relative to the pre-treatment score and does not use rescue medication. Patients who use rescue medication, discontinue prior to the 24-hour post-dose assessment, or do not achieve a $\geq 50\%$ reduction in pain score at the 24 hour post-dose assessment relative to the pre-treatment score are deemed non-responders.

The secondary efficacy variables are assessments of magnitude of pain reduction, time to response, time to complete pain relief, and interference with sleep as recorded on patient diaries by the patient. Signs and symptoms of inflammation per Investigator's clinical assessments of the target joint are evaluated. Time to drop out (use of rescue medications) is also evaluated. Investigator global assessment of response to treatment is assessed.

The primary efficacy analysis will be based on an Intent-to-Treat (ITT) population, defined as all patients who were randomized, contacted the Gout Flare Call Center, took at least one dose of study drug, and had one subsequent contact. The Per Protocol (PP) population is defined as the subset of the ITT population confirmed by the Investigator as continuing to meet all major inclusion and exclusion criteria and initiating treatment within hours of the onset of the acute gout flare. Analyses will also be made on an Evaluable patient population with an Evaluable patient defined as one who, in addition to being included in the PP population, completed the randomized treatment course. The ITT population will be used for the evaluation of safety.

Statistical tests for efficacy analysis are two-tailed with an alpha significance level of 0.05.

For primary efficacy analysis, the number of responders in the standard-dose colchicine group and the placebo group, as defined for the primary efficacy variable, will be compared using the Mantel-Haenszel chi-square test stratified on study site. The comparison of the standard-dose colchicine and placebo groups of the ITT population is the primary comparison of interest. The sensitivity to alternate definitions of response (based both on magnitude of reduction from baseline as well as time point) will be evaluated as secondary endpoints. As additional sensitivity analyses, these tests will also be repeated for the PP and Evaluable populations if the sample sizes differ from the overall ITT population by more than 10%.

For secondary efficacy analysis, the number of responders in the low-dose colchicine group will be compared to placebo and also to standard-dose colchicine using the Mantel-Haenszel chi-square test stratified on study site. Change in pain intensity, interference with sleep, time to 50% reduction in pain, and time to complete pain relief will be analyzed as continuous variables using analysis of covariance with study site, treatment group, and site by treatment interaction as independent variables for change in pain intensity and interference with sleep, with baseline score as a covariate. For the Investigator's clinical assessment of inflammation (erythema, swelling, and tenderness to touch) and Investigator's global assessment of response to treatment, the treatment groups will be compared using the Mantel-Haenszel chi-square test stratified on study site.

Safety assessments will be made based on patient and Investigator inputs. Patients will be initially screened in the clinic for inclusion by review of medical history and concomitant medication use, physical examination, measurement of vital signs (oral temperature, sitting radial or brachial pulse rate, respiratory rate, and sitting blood pressure), body weight, and clinical laboratory testing (serum biochemistry, complete blood count, and urinalysis). After randomization, clinical laboratory tests, concomitant medication use, medical history and current complaints (AE) will be reviewed every 3 months until an acute gout flare occurs in order to ensure continued eligibility. Compliance with key inclusion/exclusion criteria (based on intervening medical history and concomitant medication use) will be reconfirmed by the Gout Flare Call Center prior to authorizing the start of study drug. Following the start of study drug, patients will record any severe gastrointestinal AEs on their diaries and these will be recorded in the Case Report Form (CRF) at each clinic visit. Full physical examinations and clinical laboratory testing will be conducted at the final clinic visit (Visit 4 or Visit 5). Vital signs and body weight will be measured at each Post Flare visit (Visit 3 and 4 or 5). For those patients in whom there is an unresolved AE or clinically significant treatment emergent laboratory abnormality, there will be one additional follow up visit 14 days post flare onset (Visit 6).

Safety analysis will be performed by coding adverse events using a standardized medical dictionary and the incidence summarized by treatment group; tabulations will be prepared of all AEs as well as by relationship and by severity. Adverse events resulting in termination and events meeting regulatory criteria for seriousness will also be tabulated separately. Descriptive statistics (mean, median, standard deviation, and range) of clinical laboratory testing results and vital sign measurements will be generated for each treatment group and change from the most recent value prior to onset of the acute gout flare calculated; no inferential testing will be performed. Treatment emergent abnormalities on physical examination will be tabulated and listed by treatment group. By patient listings of all safety data and concomitant medication use will be generated.

Study Results

The following data were obtained in general accordance with the above protocol.

Out of 813 patients screened, 575 were randomized to treatment with 185 patients having a gouty flare and receiving study drug. The intent-to-treat population consisted of 184 patients (52 received standard dose, 74 received low dose and 58 received placebo).

| Number of Responders Based on Target Joint Pain Score at 24 Hours Post First Dose | | | | | |
|---|---|---|---|---|---|
| Colchicine Dose | | Placebo | Odds Ratio | | |
| Low (N = 74) | High (N = 52) | (N = 58) | (95% Confidence Intervals) | | |
| N (%) | N (%) | N (%) | Low vs. Placebo | High vs. Placebo | High vs. Low |
| 28 (37.8) | 17 (32.7) | 9 (15.5) | 3.31 (1.41, 7.77) P = 0.0046 | 2.64 (1.06, 6.62) P = 0.0343 | 0.80 (0.38, 1.68) P = 0.5529 |

| Cumulative Distribution of Degree of Percent Improvement for Target Joint Pain Score at 24 Hours Post First Dose | | | |
|---|---|---|---|
| | Colchicine Dose | | |
| % Improvement | High (N = 52) | Low (N = 74) | Placebo (N = 58) |
| >=0% | 52 (100.0%) | 74 (100.0%) | 58 (100.0%) |
| >=10% | 32 (61.5%) | 47 (63.5%) | 24 (41.4%) |
| >=20% | 29 (55.8%) | 45 (60.8%) | 21 (36.2%) |
| >=30% | 21 (40.4%) | 39 (52.7%) | 17 (29.3%) |
| >=40% | 21 (40.4%) | 36 (48.6%) | 14 (24.1%) |
| >=50% | 19 (36.5%) | 30 (40.5%) | 10 (17.2%) |
| >=60% | 15 (28.8%) | 24 (32.4%) | 7 (12.1%) |
| >=70% | 10 (19.2%) | 20 (27.0%) | 4 (6.9%) |
| >=80% | 9 (17.3%) | 15 (20.3%) | 3 (5.2%) |
| >=90% | 6 (11.5%) | 9 (12.2%) | 2 (3.4%) |
| >=100% | 6 (11.5%) | 8 (10.8%) | 2 (3.4%) |

| Treatment Response Based on at Least a 2-Unit Reduction in Target Joint Pain Score at 24 Hours and 32 Hours Post First Dose | | | | | | |
|---|---|---|---|---|---|---|
| | Number (%) of Responders | | | Treatment Comparisons | | |
| | Colchicine Dose | | | (Odds Ratio and 95% CI)[1] | | |
| Hours Post First Dose | High (N = 52) | Low (N = 74) | Placebo (N = 58) | High vs. Placebo | Low vs. Placebo | High vs. Low |
| 24 | 18 (34.6) | 32 (43.2) | 10 (17.2) | 2.54 (1.04, 6.18) p = 0.0368 | 3.66 (1.61, 8.32) p = 0.0015 | 0.69 (0.33, 1.45) p = 0.3298 |
| 32 | 20 (38.5) | 34 (45.9) | 10 (17.2) | 3.00 (1.24, 7.24) p = 0.0126 | 4.08 (1.80, 9.27) p = 0.0005 | 0.74 (0.36, 1.51) p = 0.4033 |

[1] The p-value is from the unstratified Pearson chi-square test.

| Target Joint Pain at Baseline, 24 Hours and 32 Hours Post First Dose, and Change from Baseline (LOCF) - ITT Population | | | | | | | |
|---|---|---|---|---|---|---|---|
| | | Colchicine Dose | | | Treatment Comparisons[1] | | |
| Time Point | Statistic | High (N = 52) | Low (N = 74) | Placebo (N = 58) | High vs. Placebo | Low vs. Placebo | High vs. Low |
| | | 24 Hours Post First Dose | | | | | |
| Baseline | Mean (SD) | 6.9 (1.59) | 6.9 (1.72) | 6.8 (1.44) | −1.3 p = 0.0145 | −1.5 p = 0.0055 | 0.2 p = 0.7540 |
| | Median (Mix, Max) | 7.0 (4, 10) | 7.0 (4, 10) | 7.0 (4, 10) | | | |
| Change | Mean (SD) | −2.0 (2.93) | −2.2 (3.46) | −0.7 (2.77) | | | |
| | Median (Mix, Max) | −2.0 (−9, 4) | −2.0 (−9, 5) | −0.0 (−8, 4) | | | |
| | | 32 Hours Post First Dose | | | | | |
| Baseline | Mean (SD) | 6.9 (1.59) | 6.9 (1.72) | 6.8 (1.44) | −1.6 p = 0.0057 | −1.6 p = 0.0038 | 0.1 p = 0.9238 |
| | Median (Mix, Max) | 7.0 (4, 10) | 7.0 (4, 10) | 7.0 (4, 10) | | | |
| Change | Mean (SD) | −2.3 (3.05) | −2.4 (3.59) | −0.7 (2.95) | | | |
| | Median (Mix, Max) | −2.0 (−9, 3) | −2.5 (−9, 5) | 0.0 (−8, 4) | | | |

[2] Tabled values are the difference between treatment groups mean change from baseline and p-value from ANCOVA with treatment goup as the independent variable and baseline score as the covariate.

| Total Pain Relief (TOTPAR) Based on All Target Joint Pain Scores | | | | |
|---|---|---|---|---|
| | | Colchicine Dose | | |
| Time Point | Statistic | High (N = 52) | Low (N = 74) | Placebo (N = 58) |
| Hour 24 | n | 51[1] | 74 | 58 |
| | Mean (SD) | 20.9 (48.42) | 30.5 (61.44) | 9.5 (45.87) |
| | Median(Mix, Max) | 11.5 (−102, 135) | 23.0 (−112, 185) | 7.3 (−90, 142) |

-continued

Total Pain Relief (TOTPAR) Based on All Target Joint Pain Scores

| | | Colchicine Dose | | |
|---|---|---|---|---|
| Time Point | Statistic | High (N = 52) | Low (N = 74) | Placebo (N = 58) |
| Hour 32 | n | 51 | 74 | 58 |
| | Mean (SD) | 31.9 (63.83) | 45.5 (82.05) | 12.2 (59.88) |
| | Median(Mix, Max) | 27.5 (−102, 185) | 34.1 (−128, 257) | 7.3 (−114, 142) |

[1]Patient 1026-1005 did not have a diary and the 24-hour call to the Call Center was 27 hours after the initial call. As indicated in the SAP, the Call Center pain score was not eligible for substitution for the missing diary. This patient has been excluded from the TOTPAR summary.

Number (%) of Patients Using Rescue Medication Up to and Including the 24-Hour Post First Dose Assessment

| Colchicine Dose | | | Treatment Comparison (Odds Ratio and 95% CI) | | |
|---|---|---|---|---|---|
| High (N = 52) | Low (N = 74) | Placebo (N = 58) | | | |
| n (%) | n (%) | n (%) | High vs. Placebo | Low vs. Placebo | High vs. Low |
| 18 (34.6) | 23 (31.1) | 29 (50.0%) | 0.53 (0.25, 1.14) p = 0.1034 | 0.45 (0.22, 0.92) p = 0.0273 | 1.17 (0.55, 2.50) p = 0.6768 |

Change from Baseline in Target Joint Pain Scores at 24 Hours Post First Dose with Interval of Time of Dose Relative to Flare Onset as Covariate (LOCF) - ITT Population

| | | Colchicine Dose | | | Treatment Comparisons[1] | | |
|---|---|---|---|---|---|---|---|
| | Statistic | High (N = 52) | Low (N = 74) | Placebo (N = 58) | High vs. Placebo | Low vs. Placebo | High vs. Low |
| | | Early Treatment Start (within 4 hours) | | | | | |
| Baseline | Mean (SD) | 6.9 (1.59) | 6.9 (1.72) | 6.8 (1.44) | −1.3 | −1.5 | 0.2 |
| | Median (Mix, Max) | 7.0 (4, 10) | 7.0 (4, 10) | 7.0 (4, 10) | p = 0.0145 | p = 0.0055 | p = 0.7540 |
| Change | Mean (SD) | −2.0 (2.93) | −2.2 (3.46) | −0.7 (2.77) | | | |
| | Median (Mix, Max) | −2.0 (−9, 4) | −2.0 (−9, 5) | −0.0 (−8, 4) | | | |
| | | Late Treatment Start (after 4 hours) | | | | | |
| Baseline | Mean (SD) | 6.9 (1.59) | 6.9 (1.72) | 6.8 (1.44) | −1.6 | −1.6 | 0.1 |
| | Median (Mix, Max) | 7.0 (4, 10) | 7.0 (4, 10) | 7.0 (4, 10) | p = 0.0057 | p = 0.0038 | p = 0.9238 |
| Change | Mean (SD) | −2.3 (3.05) | −2.4 (3.59) | −0.7 (2.95) | | | |
| | Median (Mix, Max) | −2.0 (−9, 3) | −2.5 (−9, 5) | 0.0 (−8, 4) | | | |

[1]Patient 1016-1013 was missing a flare onset time and Patients 1002-1007, 1018-1008, 1006-1013, 1009-1011, 1010-1005, 1010-1010, 1026-1002, 1026-1007, 1064-1007, and 1068-1022 appear to have taken the first dose of study medication prior to flare onset.
[2]Tabled values are the difference between treatment groups mean change from baseline and p-value from ANCOVA with treatment group as the independent variable and baseline score as the covariate.

Overall Summary of Treatment Emergent Adverse Events - Safety Population

| | Colchicine Dose | | |
|---|---|---|---|
| | High (N = 52) n (%) | Low (N = 74) n (%) | Placebo (N = 59) n (%) |
| Total Number of TEAEs[1] | 85 | 34 | 27 |
| Number (%) of Patients with at Least One TEAE | 40 (76.9) | 27 (36.5) | 16 (27.1) |
| Number (%) of Patients with at Least One Mild TEAE | 15 (28.8) | 19 (25.7) | 9 (15.3) |
| Number (%) of Patients with at Least One Moderate TEAE | 15 (28.8) | 8 (10.8) | 6 (10.2) |
| Number (%) of Patients with at Least One Severe TEAE | 10 (19.2) | 0 | 1 (1.7) |

Overall Summary of Treatment Emergent Adverse Events - Safety Population

| | Colchicine Dose | | |
|---|---|---|---|
| | High (N = 52) n (%) | Low (N = 74) n (%) | Placebo (N = 59) n (%) |
| Number (%) of Patients with a TEAE Discontinuing Study | 0 | 0 | 0 |
| Number (%) of Patients with a Treatment Emergent SAE | 0 | 0 | 0 |

[1]Patients reporting more than one adverse event are only counted once for a given event.

Number (%) of Patients with at Least One Treatment-Emergent Gastrointestinal Adverse Event Recorded on the Diary or the CRF- Safety Population

| | Colchicine Dose | | | | | |
|---|---|---|---|---|---|---|
| | Standard (N = 52) | | Low (N = 74) | | Placebo (N = 59) | |
| Method of Capture | All | Severe | All | Severe | All | Severe |
| Captured on Adverse Event CRF[1] | 40 (76.9)[2] | 10 (19.2) | 19 (25.7) | 0 | 12 (20.3) | 0 |
| Captured on Patient Diary | 48 (92.3)[2] | 13 (25.0) | 32 (43.2)[3] | 3 (4.1) | 15 (25.4) | 2 (3.4) |
| Captured on Patient Diary or Adverse Event CRF | 49 (94.2)[2] | 18 (34.6) | 33 (44.6) | 3 (4.1) | 16 (27.1) | 2 (3.4) |

[1]Gastrointestinal adverse events captured on the AE CRF include the MedDRA preferred terms of "diarrhoea", "nausea", "vomiting", "abdominal pain", or "abdominal pain lower", "abdominal pain upper", "abdominal discomfort", or "dyspepsia".
[2]Statistically significantly different from placebo and from Low-dose colchicine (95% CI of odds ratio does not include "1").
[3]Statistically significantly different from placebo (95% CI of odds ratio does not include "1").

Number (%) of Patients with at Least One Severe TEAE in Any Treatment Group- Safety Population

| | Colchicine Dose | | | Placebo | Odds Ratio (95% Confidence) | | |
|---|---|---|---|---|---|---|---|
| MedDRA System Organ Class / MedDRA Preferred Term | High (N = 52) n (%) | Low (N = 74) n (%) | All Colchicine (N = 126) n (%) | (N = 59) n (%) | High vs. Placebo | Low vs. Placebo | High vs. Low |
| Number of Patients with at Least One Severe TEAE | 10 (19.2) | 0 | 10 (7.9) | 1 (1.7) | 13.8 (1.7, 112) | — | — |
| Gastrointestinal Disorders | 10 (19.2) | 0 | 10 (7.9) | 0 | — | — | — |
| Diarrhea | 10 (19.2) | 0 | 10 (7.9) | 0 | — | — | — |
| Melaena | 1 (1.9) | 0 | 1 (0.8) | 0 | — | — | — |
| Nausea | 1 (1.9) | 0 | 1 (0.8) | 0 | — | — | — |
| Metabolism and Nutrition Disorders | 0 | 0 | 0 | 1 (1.7) | — | — | — |
| Gout | 0 | 0 | 0 | 1 (1.7) | — | — | — |
| Musculoskeletal and Connective Tissue Disorders | 1 (1.9) | 0 | 1 (0.8) | 0 | — | — | — |
| Pain in Extremity | 1 (1.9) | 0 | 1 (0.8) | 0 | — | — | — |

Number (%) of Patients with at Least One Drug-Related Treatment Emergent Adverse Events with an Incidence of ≧2% of Patients in Any Treatment Group

| | Colchicine Dose | | Placebo | Odds Ratio (95% Confidence Intervals) | | |
|---|---|---|---|---|---|---|
| MedDRA System Organ Class<br>MedDRA Preferred Term | High (N = 52)<br>n (%) | Low (N = 74)<br>n (%) | (N = 59)<br>n (%) | High vs.<br>Placebo | Low vs.<br>Placebo | High vs.<br>Low |
| Number of Patients with at Least One Drug-Related TEAE | 38 (73.1) | 21 (28.4) | 14 (23.7) | 8.7<br>(3.7, 20.6) | 1.3<br>(0.6, 2.8) | 6.9<br>(3.1, 15.2) |
| Gastro-intestinal Disorders | 38 (73.1) | 18 (24.3) | 11 (18.6) | 11.8<br>(4.8, 29.0) | 1.4<br>(0.6, 3.3) | 8.4<br>(3.8, 19.0) |
| Diarrhea | 38 (73.1) | 16 (21.6) | 8 (13.6) | 17.3<br>(6.6, 45.4) | 1.8<br>(0.7, 4.4) | 9.8<br>(4.3, 22.5) |
| Nausea | 7 (13.5) | 3 (4.1) | 3 (5.1) | 2.9<br>(0.7, 11.9) | 0.8<br>(0.2, 4.1) | 3.7<br>(0.9, 15.0) |
| Vomiting | 8 (15.4) | 0 | 0 | — | — | — |

As shown in the above tables, standard dose colchicine produced ≧50% pain reduction at 24 hrs without pain rescue in a greater proportion of patients than did placebo (32.7% vs. 15.5%, p=0.0343; odds ratio 2.64 (95% CI, 1.06, 6.62), and more gastrointestinal side effects than placebo (73.1% vs. 18.6%, odds ratio 11.8 {95% CI, 4.8, 29.0}), in particular more diarrhea than placebo (73.1% vs. 13.6%, odds ratio 17.3 {95% CI, 6.6, 45.4}). Low dose colchicine also produced ≧50% pain reduction at 24 hrs without pain rescue in a greater proportion of patients than did placebo (37.8% vs. 15.5%, p=0.0046; odds ratio 3.31 (95% CI, 1.41, 7.77)), and more gastrointestinal side effects than placebo (24.3% vs. 18.6%, odds ratio 1.4 {95% CI, 0.7 to 11.9}), but did not significantly differ from placebo with respect to diarrhea (21.6% vs. 13.6%, odds ratio 1.8 {95% CI, 0.7 to 4.4}). Severe diarrhea occurred in 19.2% of patients taking high-dose colchicine while not occurring in the low-dose colchicine group. Vomiting occurred in 15.4% of patients taking high-dose colchicine while not occurring in the low-dose colchicine group.

Based on the primary efficacy variable of ≧50% pain reduction at 24 hrs without pain rescue, the proportion of responders to the standard dose and the low dose colchicine regimens was not significantly different (p=0.5529). The odds ratio for being a responder to standard dose colchicine vs. being a responder to low dose colchicine was 0.80 (95% CI, 0.38, 1.68). The proportion of patients rescued prior to 24 hours for the standard dose, low dose and placebo were 34.6%, 28.4% and 48.3%, respectively.

FIG. 1 summarizes efficacy data from the trial. FIG. 1 shows the fraction of all patients improved at 24 hrs post-first dose, regardless of pain rescue, as a function of the percent improvement in pain for each of the three treatment methods (standard dose, low dose, placebo). For example, 49% of patients taking the low dose achieved at least 40% relief compared to 24% of the patients on placebo.

Standard dose oral colchicine was established to be effective, but burdened by significant diarrhea. In contrast, although low dose colchicine was not significantly different from standard dose colchicine in efficacy, low dose colchicine was not significantly different from placebo with respect to diarrhea. This trial provides a new evidence basis for acute gout treatment, specifically supporting the unexpected superiority of a low dose colchicine dosing regimen of 2 tablets of 0.6 mg followed in 1 hour by 1 tablet. The higher standard dose colchicine dosing regimen did not improve patient outcome, but did increase adverse events.

Example 4

Pharmacokinetic Study in Healthy Adults of Single vs. Multiple Oral Doses of Colchicine Tablets This study was a single-center, open-label, single-sequence, two-period study to evaluate the pharmacokinetic profile of colchicine following single and multiple oral doses of colchicine tablets, 0.6 mg, in healthy volunteers.

In Period 1, study subjects received a 0.6-mg dose of colchicine after an overnight fast of at least 10 hours. In Period 2, subjects received a 0.6-mg dose of colchicine in the morning and the evening (approximately 12 hours later) for 10 days (steady state regimen). Subjects received a light breakfast served 60 minutes following dose administration in the morning and the evening dose was administered 90 minutes after an evening meal on Days 15 through 24 only. On Day 25, the colchicine dose was administered after an overnight fast of at least 10 hours and lunch was served 4 hours post-dose. Study periods were separated by a 14-day washout. Following the single dose and the last dose of the multiple dose regimen (beginning on the mornings of Day 1 and Day 25, respectively), blood samples were collected (6 mL each) from each subject within 1 hour prior to dosing and after dose administration at study hours 0.5, 1, 1.5, 2, 3, 4, 6, 8, 10, 12, and 24 (while confined) and 36, 48, 72, and 96 (on an outpatient basis). Plasma concentrations of colchicine and its metabolites were determined using validated LC/MS-MS methods.

Thirteen healthy, non-smoking subjects with a mean age of 25.5 years (range 19 to 38 years) and within 15% of ideal body weight were enrolled in this study. All subjects completed both dosing periods according to protocol.

After a single dose, plasma concentrations are no longer quantifiable 24 hours post-dose in all but 1 subject. After the last dose of the steady state regimen, concentrations remained quantifiable for 48 to 72 hours. Review of individual subject data shows that no subject experienced a secondary colchicine peak, either following a single dose or upon multiple dosing.

All 2-O-demethylcolchicine (2-DMC) concentrations were below the level of quantitation (LOQ, 0.2 ng/mL) and only one sample from 1 subject (of 13 subjects) had a detectable 3-O-demethylcolchcine (3-DMC) concentration which was near the level of quantitation. Therefore, metabolites are not discussed further.

In healthy adults, colchicine appears to be readily absorbed when given orally, reaching a mean maximum plasma concentration of 2.5 ng/mL in 1.5 hours after a single dose. The drug is distributed widely, with an apparent volume of distribution of 540 L, greatly exceeding total body water. The elimination half-life as calculated following a single oral dose is approximately 5 hours. Levels were not detectable by 24 hours post-dose and this is therefore not an accurate estimate. Pharmacokinetic parameter values are summarized in the table below.

Review of trough plasma concentrations indicates that steady state was attained by approximately the eighth day of dosing for most subjects. Colchicine may have a diurnal variation reflected in the observed Cmin concentrations at steady state. Cmin concentrations prior to the morning dose are approximately 12% higher than the Cmin concentrations prior to the evening dose (Day 23 and Day 24). The mean Cmin concentration observed on Day 25 was 0.907 ng/mL.

Colchicine accumulated following administration of multiple doses to an extent greater than expected. Exposure was nearly two-fold higher (approximately 1.7 based on AUC [Day 25 $AUC_{0-\tau}$/Day 1 $AUC_{0-\infty}$] and approximately 1.5 based on Cmax [Day 25 $C_{max}$/Day 1 $C_{max}$]). This observation could be attributable to an underestimation of AUC∞ following a single dose. With the higher plasma levels that occur with repeated dosing, a longer terminal elimination half life is apparent, 26.6 hours. Pharmacokinetic parameter values are summarized in the tables below.

TABLE 10

Colchicine Pharmacokinetic Parameter Values Following Administration of A Single Oral Dose of Colchicine 0.6 mg in Healthy Adults

|        | $AUC_{0-t}$ (pg-hr/mL) | $AUC_{0-inf}$ (pg-hr/mL) | $C_{max}$ (pg/mL) | $T_{max}$ (hr) | Kel (1/hr) | $T_{1/2}$ (hr) |
|--------|------------------------|--------------------------|-------------------|----------------|------------|----------------|
| N      | 13        | 13        | 13      | 13    | 13     | 13    |
| MEAN   | 10508.54  | 12281.90  | 2470.77 | 1.50  | 0.1829 | 4.95  |
| STDEV  | 3544.82   | 4423.34   | 706.98  | 0.54  | 0.0592 | 4.43  |
| % CV   | 33.73     | 36.02     | 28.61   | 36.00 | 32.39  | 89.54 |
| MEDIAN | 10560.90  | 11451.45  | 2714.00 | 1.50  | 0.1992 | 3.48  |
| MIN    | 4812.88   | 7252.66   | 1584.00 | 1.00  | 0.0359 | 2.84  |
| MAX    | 18128.65  | 23838.48  | 3977.00 | 3.00  | 0.2443 | 19.29 |

TABLE 11

Colchicine Pharmacokinetic Parameter Values Following Administration of Multiple (b.i.d.) Oral Doses of Colchicine 0.6 mg in Healthy Adults

|        | $AUC_{0-t}$ (pg-hr/mL) | $AUC_{0-\tau}$ (pg-hr/mL) | $AUC_{0-inf}$ (pg-hr/mL) | $C_{max}$ (pg/mL) | $C_{min}$ (pg/mL) | $C_{ave}$ (pg/mL) | $T_{max}$ (hr) | Kel (1/hr) | $T_{1/2}$ (hr) |
|--------|----------|----------|----------|---------|---------|---------|-------|-------|-------|
| N      | 13       | 13       | 13       | 13      | 13      | 13      | 13    | 13    | 13    |
| MEAN   | 43576.96 | 29056.23 | 54198.77 | 3553.15 | 906.51  | 1210.68 | 1.31  | 0.03  | 26.60 |
| STDEV  | 9333.26  | 4531.30  | 9214.54  | 843.45  | 152.19  | 188.80  | 0.60  | 0.00  | 4.33  |
| % CV   | 21.42    | 15.59    | 17.00    | 23.74   | 16.79   | 15.59   | 45.61 | 16.34 | 16.26 |
| MEDIAN | 41925.10 | 28452.15 | 54113.43 | 3734.00 | 903.50  | 1185.51 | 1.00  | 0.03  | 26.51 |
| MIN    | 29328.78 | 20791.98 | 37599.76 | 1977.00 | 636.23  | 866.33  | 0.50  | 0.02  | 20.82 |
| MAX    | 58265.35 | 36083.95 | 67944.65 | 4957.00 | 1149.67 | 1503.50 | 3.00  | 0.03  | 33.65 |

TABLE 12

Mean (% CV) Colchicine Pharmacokinetic Parameter Values Following Administration of Single and Multiple (b.i.d.) Oral Doses of Colchicine 0.6 mg in Healthy Adults

|        | Vd/F(L) | CL/F (L/hr) |
|--------|---------|-------------|
| Colchicine 0.6-mg Single Dose (N = 13) | | |
| Day 1  | 341 (54.4) | 54.1 (31.0) |
| Colchicine 0.6 mg b.i.d. × 10 days | | |
| Day 25 | 1150 (18.73) | 30.3 (19.0) |

CL = Dose/$AUC_{0-t}$ (Calculated from mean values)
Vd = CL/Ke (Calculated from mean values)

In the above table, the parameter CL/F denotes the apparent total body clearance after administration, calculated as Total Dose/Total $AUC0\text{-}_{tau}$; and $V_d/F$ denotes the apparent total volume of distribution after administration, calculated as Total Dose/(Total $AUC_\infty \times K_{el}$).

Example 5

Pharmacokinetic Study in Healthy Adults of Low Dose Acute Gout Regimen: 1.8 mg Over 2 Hours This study was a single-center, single-period, open-label pharmacokinetic study conducted in healthy subjects under fasting conditions. It was designed to characterize the pharmacokinetic profile of a low-dose regimen of colchicine (1.8 mg over 2 hours) used as one of the treatment arms in the randomized, controlled trial in patients with an acute gout flare discussed above.

Thirteen healthy, non-smoking subjects with a mean age of 29.3 years (range 20 to 49 years) and within 15% of ideal body weight were enrolled in this study. Subjects received 2×0.6 mg tablets initially followed by 1×0.6 mg tablet 1 hour later. Blood samples for measurement of colchicine plasma concentrations and metabolites were collected (relative to the first dose of study drug) at pre-dose; 0.5 and 1 hour post-dose (prior to second dose); and 1.5, 2, 2.5, 3, 4, 6, 8, 12, 18, 24, 36, and 48 hours post-dose. Subjects were confined until 48 hours post-dose and then returned 72 and 96 hours after the first dose for additional blood sampling on an outpatient basis. Plasma concentrations of colchicine and its metabolites were determined using validated LC/MS-MS methods.

2-DMC concentrations were below the LOQ for all subjects. Eight of 13 subjects had at least one measurable 3-DMC concentration (29 total 3-DMC measurable concentrations). 3-DMC concentrations ranged from 0.20 ng/mL (near the LOQ) to 0.45 ng/mL and were observed 1 to 4 hours post-dose. Given these low levels, metabolites are not discussed further herein.

When colchicine was administered in this low-dose regimen, concentrations increased to a maximum of 6.2 ng/mL, occurring 1.81 hours after the initial dose (0.81 hours after the second dose). Most of the subjects (10 of 13 subjects or 77%) experienced a secondary peak within 6 hours after the first of the two doses, attributed to intestinal secretion and re-absorption and/or biliary recirculation.

The terminal elimination half-life was 23.6 hours. A summary of the pharmacokinetic parameter values is provided in the table below.

TABLE 12

COLCHICINE PHARMACOKINETIC PARAMETER VALUES AFTER LOW-DOSE COLCHICINE (1.8 MG OVER 2 HOURS) ADMINISTRATION IN HEALTHY ADULTS

|  | $C_{max}$ (pg/mL) | $T_{max}$ (hr) | Total $AUC_{0-t}$ (pg-hr/mL) | Total $AUC_\infty$ (pg-hr/mL) | $K_{el}$ (1/hr) | CL/F (mL/hr) | $V_{area}/F$ (L) | $t_{1/2}$ (hr) |
|---|---|---|---|---|---|---|---|---|
| N | 13 | 13 | 13 | 13 | 13 | 13 | 13 | 13 |
| MEAN | 6192.77 | 1.81 | 43787.55 | 52070.06 | 0.0326 | 36950.93 | 1188.72 | 23.63 |
| STDEV | 2433.70 | 0.38 | 11437.48 | 13689.27 | 0.0100 | 9993.17 | 319.56 | 9.24 |
| % CV | 39.30 | 21.24 | 26.12 | 26.29 | 30.80 | 27.04 | 26.88 | 39.10 |
| MEDIAN | 5684.00 | 2.00 | 43942.15 | 50783.77 | 0.0322 | 35444.40 | 1149.35 | 21.56 |
| MIN | 3160.00 | 1.00 | 28821.45 | 34171.00 | 0.0141 | 24295.73 | 774.19 | 13.80 |
| MAX | 11370.00 | 2.50 | 58931.99 | 74087.08 | 0.0502 | 52676.24 | 1724.36 | 49.20 |

Example 6

Pharmacokinetic Study in Healthy Adults of a Standard-Dose Acute Gout Regimen: 4.8 mg Colchicine over 6 Hours This study was a single center, randomized, double-blind, double-dummy pharmacokinetic and exploratory ECG safety study.

With respect to the pharmacokinetic aspect of the study, on Day 1, following a minimum of 10 hours overnight fast, subjects received the appropriate randomized study drug (combination of over-encapsulated active drug or placebo capsules such that the blind was preserved). Those randomized to colchicine received 4.8 mg over 6 hours (initially 2×0.6 mg tablets followed by 1×0.6 mg tablet every hour for six additional doses). Those randomized to moxifloxacin received 1×400 mg tablet. Both dosing regimens were followed by a 4-hour post-dose fast (post-dose fast for colchicine arm started after the first dose of colchicine administered). Blood samples were obtained on Day 1 at the following time points (relative to the first dose of study drug): pre-dose and 1 (prior to second dose), 3 (prior to fourth dose), 6 (prior to final dose), 6.17, 6.33, 6.5, 6.75, 7, 7.25, 7.5, 7.75, 8, 10, 12, 23, 36, 48, 72 and 96 hours post-dose. Subjects were confined until 48 hours post-dose and then returned 72 and 96 hours after the first dose for additional blood sampling on an outpatient basis. Plasma concentrations of colchicine and its metabolites were determined using validated LC/MS-MS methods.

Eighteen healthy, non-smoking subjects with a mean age of 28.7 years (range 18 to 50 years) and within 15% of ideal body weight were enrolled in this study. Fifteen subjects were randomized to receive colchicine and 3 subjects were randomized to receive moxifloxacin as a positive control for QTc prolongation. All subjects completed the study according to protocol.

When colchicine was administered as the standard-dose regimen used in the treatment of patients experiencing an acute gout flare, colchicine concentrations increased to a maximum of 6.8 ng/mL (similar to the reported Cmax in the low-dose regimen) and absorbed approximately 4.5 hours after the initial dose (3.5 hours after the second dose). Most of the subjects (13 of 15 subjects receiving colchicine or 87%) experienced a secondary peak within 6 hours after a single oral dose, attributed to intestinal secretion and re-absorption and/or biliary recirculation. The terminal elimination half-life was 31.38 hours. A summary of the pharmacokinetic parameter values is provided in the table below.

TABLE 13

MEAN (% CV) COLCHICINE PHARMACOKINETIC PARAMETER VALUES AFTER STANDARD-DOSE COLCHICINE (4.8 MG OVER 6 HOURS) ADMINISTRATION IN HEALTHY ADULTS

|  | $C_{max}$ (ng/mL) | $T_{max}$ (hr) | Total $AUC_{0-t}$ (ng-hr/mL) | Total $AUC_\infty$ (ng-hr/mL) | $K_{el}$ ($h^{-1}$) | CL/F (mL/hr) | $V_{area}/F$ (L) | $t_{1/2}$ (hr) |
|---|---|---|---|---|---|---|---|---|
| N | 15 | 15 | 15 | 15 | 15 | 15 | 15 | 15 |
| MEAN | 6.84 | 4.47 | 104.95 | 118.20 | 0.0242 | 43168.87 | 1876.09 | 31.38 |
| STDEV | 1.30 | 1.99 | 24.61 | 26.01 | 0.0088 | 12862.03 | 456.19 | 8.36 |
| % CV | 18.94 | 44.65 | 23.45 | 22.01 | 36.59 | 29.79 | 24.32 | 26.65 |
| MEDIAN | 6.69 | 3.12 | 113.12 | 126.47 | 0.0212 | 37954.71 | 1902.14 | 32.76 |
| MIN | 4.95 | 3.12 | 53.74 | 61.31 | 0.0147 | 31386.01 | 805.92 | 15.03 |
| MAX | 8.60 | 7.50 | 138.24 | 152.93 | 0.0461 | 78287.41 | 2639.21 | 47.22 |

2-DMC concentrations were below LOQ for all subjects. Fourteen of 15 subjects had at least one measurable 3-DMC concentration; the 3-DMC concentrations ranged from 0.25 ng/mL (near the LOQ) to 0.42 ng/mL and were observed 1.12 to 12.12 hours post-dose. Summary mean 3-DMC pharmacokinetic parameter values can be found in the table below. The observed mean 3-DMC Cmax, AUC0-t, and AUC∞ concentrations were approximately 4.7%, 2%, and 4.1% of the observed mean colchicine Cmax, AUC0-t, AUC∞ concentrations, respectively.

TABLE 14

Mean (% CV) 3-DMC Pharmacokinetic Parameter Values after Standard-Dose Colchicine (4.8 mg over 6 hours) Administration in Healthy Adults

|  | $C_{max}$ (ng/mL) N = 15 | $T_{max}$[1] (h) N = 14 | $AUC_{0-t}$ (ng·h/mL) N = 13 | $AUC_\infty$ (ng·h/mL) N = 8 | Ke ($h^{-1}$) N = 8 | $t_{1/2}$ (h) N = 8 |
|---|---|---|---|---|---|---|
| Standard Dose N = 15 | 0.32 (16.35) | 5.06 (3.12-8.12) | 2.09 (40.29) | 4.84 (42.73) | 0.1418 (60.15) | 6.93 (64.35) |

[1] $T_{max}$ reported mean (range)

Example 7

Food Effect Study Single Dose vs. COL-PROBENECID® (0.5 mg Colchicine/500 mg Probenecid)

The clinical study of this example was a randomized, single-dose, three-way crossover study testing the bioequivalence of two formulations of colchicine administered under standard fasting conditions, one the 0.6 mgA colchicine formulation of Example 2 (test product) and one a marketed combination product, 0.5 mg colchicine/500 mg probenecid tablets (COL-PROBENECID®, Watson Laboratories, Inc.) (reference product), and the effect of food on the test product by dosing following a high-fat breakfast.

Twenty-eight healthy non-smoking adult volunteers (male and female) and no alternates initiated the study. Subjects received three single doses, in a randomized sequence of three treatment periods. On each occasion, subjects received either one colchicine tablet USP, 0.6 mg (test product) given either with food or in a standard fasting condition or one colchicine 0.5 mg/probenecid 500 mg tablet (reference product) given in a standard fasting condition. Each treatment period was separated by a 14-day washout.

The two dosing conditions were (1) Standard Fasting Conditions (either colchicine tablets USP, 0.6 mg (test A) or reference product, COL-PROBENECID®): 1 tablet of test product (Test A) or reference product with 240 mL of room temperature water after an overnight fast of at least 10 hours; subjects will continue to fast for 4 hours post-dose; and (2) High-fat Breakfast (colchicine tablets USP, 0.6 mg): 1 tablet of test product (Test B) with 240 mL of room temperature water 30 minutes after initiation of a standardized, high-fat and high-calorie breakfast (FDA standard meal) preceded by an overnight fast.

Subjects were confined for at least 15 hours prior to and until at least 24 hours after dosing each period. During each period, subjects returned on four separate occasions for outpatient blood sampling.

No fluid, except that given with drug administration and the standardized high-fat and high-calorie breakfast (FDA standard meal) depending on the randomization, was allowed from 1 hour prior to dose administration until 2 hours after dosing. When fluids were restricted, they will be allowed ad libitum but will generally be controlled.

Dinner was served approximately 13.5 hours prior to dose administration. At 30 minutes before dose administration, those subjects to be dosed after eating (depending on randomization) were served the standardized, high-fat and high-calorie breakfast (FDA standard meal). All subjects fasted for at least 4 hours after dosing. Clear fluids, such as water, were allowed during fasting.

Subjects were served standardized meals and beverages, controlled by the clinic during periods of confinement. Meals were the same in content and quantity during each confinement period. No grapefruit and/or grapefruit containing products or caffeine and/or xanthine containing products were allowed during the confinement portions of the study.

During confinement, only non-strenuous activity was permitted. Following dose administration, subjects remained in a seated or upright position for at least 4 hours to ensure proper gastric emptying and subject safety.

Blood (6 mL) was collected in K2 EDTA vacutainers with samples taken within 1 hour prior to dosing (0 hour) and after dose administration at 0.5, 1, 1.5, 2, 3, 4, 6, 8, 12, and 24 hours (while confined) and 36, 48, 72, and 96 hours (on an outpatient basis). 1. Colchicine and metabolite plasma concentrations (colchicine, 2-DMC, 3-DMC, and 10 demethylcolchicine) were measured using a validated bioanalytical method.

Pharmacokinetic results comparing the test product under fed and fasting conditions are shown below.

TABLE 15

Pharmacokinetic results of colchicine test product under fed and fasting

| | Ln-Transformed Data | | | | | |
|---|---|---|---|---|---|---|
| | Least Squares Mean | | Geometric Mean | | | 90% Confidence Interval (Lower Limit, |
| PK Variable | Test B | Test A | Test B | Test A | % Ratio | Upper Limit) |
| $C_{max}$ (ng/mL) | 7.784 | 7.781 | 2402.55 | 2393.60 | 100.37 | (89.84, 112.14) |
| $AUC_{0-t}$ (ng/mL-hr) | 9.201 | 9.334 | 9906.40 | 11310.90 | 87.58 | (78.07, 98.26) |
| $AUC_{0-inf}$ (ng/mL-hr) | 9.300 | 9.468 | 10939.73 | 12939.64 | 84.54 | (76.73, 93.15) |

Geometric means are based on least squares means of ln-transformed values.

TABLE 15-continued

| | Non-Transformed Data | | | |
|---|---|---|---|---|
| | Least Squares Mean | | | 90% Confidence Interval |
| PK Variable | Test B | Test A | % Ratio | (Lower Limit, Upper Limit) |
| $C_{max}$ (pg/mL) | 2486.99 | 2493.15 | 99.75 | (90.43, 109.07) |
| $AUC_{0-t}$ (pg/mL-hr) | 10438.89 | 12536.56 | 83.27 | (72.79, 93.74) |
| $AUC_{0-inf}$ (pg/mL-hr) | 11345.62 | 13907.83 | 81.58 | (71.53, 91.63) |
| $T_{max}$ (hr) | 1.85 | 1.35 | 137.14 | (111.11, 163.17) |
| Kel (hr$^{-1}$) | 0.1902 | 0.1520 | 125.13 | (107.67, 142.58) |
| $T_{1/2}$ (hr) | 4.34 | 6.27 | 69.17 | (45.2, 93.14) |

TABLE 16

Descriptive statistics for Pharmacokinetic Parameters for Test Product A (0.6 mg) - Fasting conditions

| | AUC0-t (pg-hr/mL) | AUC0-inf (pg-hr/mL) | Cmax (pg/mL) |
|---|---|---|---|
| N | 25 | 24 | 25 |
| Arithmetic Mean | 12589 | 14113 | 2503 |
| STDev | 6210.729 | 5595.398 | 722.049 |
| % CV | 48.621 | 39.648 | 28.847 |
| Median | 11412.80 | 12756.02 | 2473.00 |
| Min | 4430.73 | 6674.96 | 1291.00 |
| Max | 30787.30 | 27789.51 | 3989.00 |

TABLE 17

Descriptive statistics for Pharmacokinetic Parameters for Test Product A (0.6 mg) - Fed conditions

| | AUC0-t (pg-hr/mL) | AUC0-inf (pg-hr/mL) | Cmax (pg/mL) |
|---|---|---|---|
| N | 25 | 22 | 25 |
| Arithmetic Mean | 10491 | 11404 | 2497 |
| STDev | 4024.804 | 2895.681 | 695.091 |
| % CV | 38.374 | 25.392 | 27.838 |
| Median | 9556.25 | 10964.17 | 2293.00 |
| Min | 6168.53 | 7128.50 | 1256.00 |
| Max | 26031.15 | 20101.33 | 3930.00 |

Food was observed to have negligible effect on rate of absorption, as indicated by the percent ratio of ln-transformed Cmax data of 100.37, but decreased the extent of absorption by about 15%, as indicated by the percent ratio of ln-transformed AUC0-t and AUC0-inf values of 87.56 and 84.54, respectively. Under fasted and fed conditions, the mean Cmax was 2.5 ng/mL. Tmax was 1.35 hrs under fasted conditions and 1.85 hrs under fed conditions.

Pharmacokinetic results comparing the test product to the reference product are shown in the tables below. The difference in colchicine potency of the test and reference products was corrected by calculating dose-normalized values in the pharmacokinetic parameters.

TABLE 18

Summary of Statistical Analysis Colchicine Test Product A (0.6 mg) - Fasting vs Reference Product C (0.5 mg) - Fasting (Dose Normalized to 0.5 mg) N = 25

| | Ln-Transformed Data | | | | | |
|---|---|---|---|---|---|---|
| | Least Squares Mean | | Geometric Mean | | | 90% Confidence Interval (Lower Limit, |
| PK Variable | Test A | Reference C | Test A | Reference C | % Ratio | Upper Limit) |
| $C_{max}$ (pg/mL) | 7.598 | 7.374 | 1994.67 | 1594.51 | 125.10 | (111.97, 139.76) |
| $AUC_{0-t}$ (pg/mL-hr) | 9.151 | 8.833 | 9425.75 | 6858.61 | 137.43 | (122.5, 154.18) |
| $AUC_{0-inf}$ (pg/mL-hr) | 9.286 | 8.970 | 10783.03 | 7863.34 | 137.13 | (124.46, 151.09) |

Geometric means are based on least squares means of ln-transformed values.

| | Non-Transformed Data | | | |
|---|---|---|---|---|
| | Least Squares Mean | | | 90% Confidence Interval |
| PK Variable | Test A | Reference C | % Ratio | (Lower Limit, Upper Limit) |
| $C_{max}$ (pg/mL) | 2076.08 | 1688.54 | 122.95 | (110.07, 135.83) |
| $AUC_{0-t}$ (pg/mL-hr) | 10435.91 | 8016.44 | 130.18 | (115.25, 145.11) |
| $AUC_{0-inf}$ (pg/mL-hr) | 11565.28 | 8230.68 | 140.51 | (126.04, 154.99) |
| $T_{max}$ (hr) | 1.35 | 1.34 | 100.11 | (74.05, 126.17) |
| Kel (hr$^{-1}$) | 0.1520 | 0.1970 | 77.16 | (63.69, 90.63) |
| $T_{1/2}$ (hr) | 6.27 | 3.78 | 165.89 | (126.13, 205.65) |

The 0.6 mgA colchicine tablet, formulated as in Example 2, showed enhanced bioavailability over COL-PROBENECID®. The formulation disclosed herein showed a greater rate and extent of absorption than did the COL-PROBENECID®.

Recitation of ranges of values herein are merely intended to serve as a shorthand method of referring individually to each separate value falling within the range, unless otherwise indicated herein, and each separate value is incorporated into the specification as if it were individually recited herein. The endpoints of all ranges directed to the same component or property are inclusive and independently combinable.

All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs. The terms wt %, weight percent, percent by weight, etc. are equivalent and interchangeable.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A method of treating a gout flare with colchicine in a patient undergoing colchicine prophylactic treatment of gout flares, consisting of
   administering to a patient having a gout flare while undergoing prophylactic treatment of gout flares
   1.2 mgA oral colchicine at the onset of the acute gout flare, followed by 0.6 mgA oral colchicine about one hour later; and
   after waiting 12 hrs, continuing prophylactic treatment consisting of 0.6 mgA or 1.2 mgA oral colchicine daily.

* * * * *

UNITED STATES PATENT AND TRADEMARK OFFICE
CERTIFICATE OF CORRECTION

| | | |
|---|---|---|
| PATENT NO. | : 7,981,938 B2 | Page 1 of 2 |
| APPLICATION NO. | : 12/687406 | |
| DATED | : July 19, 2011 | |
| INVENTOR(S) | : Matthew W. Davis | |

It is certified that error appears in the above-identified patent and that said Letters Patent is hereby corrected as shown below:

In column 1, line 25, delete "N-[7S," and insert -- N-[(7S, --, therefor.

In column 5, line 48, delete "mitotis," and insert -- mitosis, --, therefor.

In column 10, line 9, delete "HPLC" and insert -- UPLC --, therefor.

In column 10, line 65, "(HPLC)" and insert -- (UPLC) --, therefor.

In column 14, line 8, delete "manufacture" and insert -- manufacture. --, therefor.

In column 14, line 30, delete "N-formyldeactylcholchicine," and insert
-- N-formyldeacetylcolchicine, --, therefor.

In column 16, line 20, delete "composition" and insert -- composition. --, therefor.

In column 16, line 26, delete "alignates," and insert -- alginates --, therefor.

In column 16, line 46-47, delete "crosscarmelose" and insert -- croscarmellose --, therefor.

In column 18, line 36, delete "HPLC" and insert -- UPLC --, therefor.

In column 20, line 62, delete "0.5%" and insert -- 0.5%. --, therefor.

In column 22, line 22, delete "Buffer:methanl" and insert -- Buffer:methanol --, therefor.

In column 22, line 58, delete "Volumentric" and insert -- Volumetric --, therefor.

In column 22, line 62, delete "Volumentric" and insert -- Volumetric --, therefor.

Signed and Sealed this
Twenty-second Day of November, 2011

David J. Kappos
*Director of the United States Patent and Trademark Office*

CERTIFICATE OF CORRECTION (continued)
U.S. Pat. No. 7,981,938 B2

In column 27, line 61, delete "1βscreen" and insert -- 1A screen --, therefor.

In column 28, line 67, delete "probenicid." and insert -- probenecid. --, therefor.

In column 35, line 17, before "hours" insert -- 12 --.

In column 37-38, line 39, delete "goup" and insert -- group --, therefor.

In column 45, line 4, delete "3-O-demethylcolchcine" and insert -- 3-O-demethylcolchicine --, therefor.

UNITED STATES PATENT AND TRADEMARK OFFICE
CERTIFICATE OF CORRECTION

| | |
|---|---|
| PATENT NO. | : 7,981,938 B2 |
| APPLICATION NO. | : 12/687406 |
| DATED | : July 19, 2011 |
| INVENTOR(S) | : Matthew W. Davis |

It is certified that error appears in the above-identified patent and that said Letters Patent is hereby corrected as shown below:

In column 3, line 20, delete "Cmax" and insert -- $C_{max}$ --, therefor.

In column 4, line 24, delete "Cmax" and insert -- $C_{max}$ --, therefor.

In column 4, line 39, delete "Cmax" and insert -- $C_{max}$ --, therefor.

In column 4, line 49, delete "Cmax" and insert -- $C_{max}$ --, therefor.

In column 4, line 50, delete "Cmax" and insert -- $C_{max}$ --, therefor.

In column 13, line 49, delete "4000 mL" and insert -- 400 mL --, therefor.

In column 18, line 18, delete "Impurity B." and insert -- Impurity B, --, therefor.

In column 22, line 6, after "USP/30NF25" insert -- . --.

In column 29, line 8, delete "$^{(}$Probenecid" and insert -- (Probenicid --, therefor.

In column 31, line 29, delete "levels to undetectable" and insert -- undetectable --, therefor.

In column 34, line 10, delete "also be," and insert -- also --, therefor.

In column 37, line 54, delete "$^{2}$Tabled" and insert -- $^{1}$Tabled --, therefor.

In column 39, line 51, delete "$^{1}$Patient" and insert -- Patient --, therefor.

In column 39, line 53, delete "$^{2}$Tabled" and insert -- $^{1}$Tabled --, therefor.

In column 45, line 22, delete "Cmin" and insert -- $C_{min}$ --, therefor.

Signed and Sealed this
Third Day of July, 2012

David J. Kappos
*Director of the United States Patent and Trademark Office*

In column 45, line 23, delete "Cmin" and insert -- $C_{min}$ --, therefor.

In column 45, line 24, delete "Cmin" and insert -- $C_{min}$ --, therefor.

In column 45, line 26, delete "Cmin" and insert -- $C_{min}$ --, therefor.

In column 45, line 33, delete "AUC∞" and insert -- $AUC_{\infty}$ --, therefor.

In column 45, line 43, delete "Kel" and insert -- $K_{el}$ --, therefor.

In column 46, line 1, after "Table 12" insert -- A --.

In column 46, line 6, delete "Vd" and insert -- $V_d$ --, therefor.

In column 46, line 14, delete "Vd = CL/Ke" and insert -- $V_d = CL/K_e$ --, therefor.

In column 46, line 17, delete "AUC0-tau" and insert -- $AUC_{0-tau}$ --, therefor.

In column 46, line 59, delete "Kel" and insert -- $K_{el}$ --, therefor.

In column 47, line 12, after "Table 12" insert -- B --.

In column 48, line 33, delete "Cmax" and insert -- $C_{max}$ --, therefor.

In column 48, line 64, delete "Cmax" and insert -- $C_{max}$ --, therefor.

In column 48, line 64, delete "AUC0-t" and insert -- $AUC_{0-t}$ --, therefor.

In column 48, line 64, delete "AUC∞" and insert -- $AUC_{\infty}$ --, therefor.

In column 48, line 66, delete "Cmax" and insert -- $C_{max}$ --, therefor.

In column 48, line 66, delete "AUC0-t" and insert -- $AUC_{0-t}$ --, therefor.

In column 48, line 66, delete "AUC∞" and insert -- $AUC_{\infty}$ --, therefor.

In column 49, line 5, delete "Ke" and insert -- $K_e$ --, therefor.

In column 49, line 63, delete "ng" and insert -- pg --, therefor.

In column 49, line 64, delete "ng" and insert -- pg --, therefor.

In column 49, line 65, delete "ng" and insert -- pg --, therefor.

CERTIFICATE OF CORRECTION (continued)
U.S. Pat. No. 7,981,938 B2

In column 50, line 66, delete "In-transformed" and insert -- ln-transformed --, therefor.

In column 51, line 11, delete "Kel" and insert -- $K_{el}$ --, therefor.

In column 51, line 19, delete "AUC0-t" and insert -- $AUC_{0-t}$ --, therefor.

In column 51, line 19, delete "AUC0-inf" and insert -- $AUC_{0-inf}$ --, therefor.

In column 51, line 20, delete "Cmax" and insert -- $C_{max}$ --, therefor.

In column 51, line 34, delete "AUC0-t" and insert -- $AUC_{0-t}$ --, therefor.

In column 51, line 34, delete "AUC0-inf" and insert -- $AUC_{0-inf}$ --, therefor.

In column 51, line 35, delete "Cmax" and insert -- $C_{max}$ --, therefor.

In column 51, line 64, delete "Kel" and insert -- $K_{el}$ --, therefor.

In column 52, line 19, delete "AUC0-t" and insert -- $AUC_{0-t}$ --, therefor.

In column 52, line 19, delete "AUC0-inf" and insert -- $AUC_{0-inf}$ --, therefor.

In column 52, line 20, delete "Cmax" and insert -- $C_{max}$ --, therefor.

In column 52, line 28, delete "Cmax" and insert -- $C_{max}$ --, therefor.

In column 52, line 30, delete "AUC0-t" and insert -- $AUC_{0-t}$ --, therefor.

In column 52, line 30, delete "AUC0-inf" and insert -- $AUC_{0-inf}$ --, therefor.

In column 52, line 31, delete "Cmax" and insert -- $C_{max}$ --, therefor.

In column 52, line 32, delete "Tmax" and insert -- $T_{max}$ --, therefor.